(12) United States Patent
Sapiens et al.

(10) Patent No.: US 9,915,524 B2
(45) Date of Patent: Mar. 13, 2018

(54) OPTICAL METROLOGY WITH SMALL ILLUMINATION SPOT SIZE

(71) Applicant: KLA-Tencor Corporation, Milpitas, CA (US)

(72) Inventors: Noam Sapiens, Cupertino, CA (US); Kevin A. Peterlinz, San Ramon, CA (US); Alexander Buettner, Weilburg (DE); Kerstin Purrucker, Fliederweg (DE); Andrei V. Shchegrov, Campbell, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 110 days.

(21) Appl. No.: 14/708,454

(22) Filed: May 11, 2015

(65) Prior Publication Data

US 2016/0334326 A1    Nov. 17, 2016

(51) Int. Cl.
| | | |
|---|---|---|
| *G01N 21/21* | (2006.01) | |
| *G01B 11/24* | (2006.01) | |
| *G03F 7/20* | (2006.01) | |
| *G01N 21/956* | (2006.01) | |

(52) U.S. Cl.
CPC .......... *G01B 11/24* (2013.01); *G03F 7/70625* (2013.01); *G01B 2210/56* (2013.01); *G01N 21/956* (2013.01); *G01N 2021/213* (2013.01)

(58) Field of Classification Search
CPC . G01B 11/24; G01B 2210/56; G03F 7/70625; G01N 21/956; G01N 2021/213
See application file for complete search history.

(56) References Cited

U.S. PATENT DOCUMENTS

| | | |
|---|---|---|
| 4,586,816 A | 5/1986 | Stewart |
| 5,608,526 A | 3/1997 | Piwonka-Corle et al. |
| 5,859,424 A | 1/1999 | Norton et al. |
| 6,429,943 B1 | 8/2002 | Opsal et al. |

(Continued)

OTHER PUBLICATIONS

International Search Report dated Aug. 17, 2016, for PCT Application No. PCT/US2016/031526 filed on May 9, 2016 by KLA-Tencor Corporation, 3 pages.

*Primary Examiner* — Dominic J Bologna
(74) *Attorney, Agent, or Firm* — Spano Law Group; Joseph S. Spano

(57) ABSTRACT

Methods and systems are presented to reduce the illumination spot size projected onto a measurement target and associated spillover onto area surrounding a measurement target. In one aspect, a spatial light modulator (SLM) is located in the illumination path between the illumination light source and the measurement sample. The SLM is configured to modulate amplitude, phase, or both, across the path of the illumination light to reduce wavefront errors. In some embodiments, the desired state of the SLM is based on wavefront measurements performed in an optical path of the metrology system. In another aspect, an illumination aperture having an image plane tilted at an oblique angle with respect to a beam of illumination light is employed to overcome defocusing effects in metrology systems that employ oblique illumination of the measurement sample. In some embodiments, the illumination aperture, objective lens, and specimen are aligned to satisfy the Scheimpflug condition.

20 Claims, 18 Drawing Sheets

(56) References Cited

U.S. PATENT DOCUMENTS

| | | | |
|---|---|---|---|
| 6,707,020 B1* | 3/2004 | Praus, II | G01J 9/00 250/201.9 |
| 7,478,019 B2 | 1/2009 | Zangooie et al. | |
| 7,933,026 B2 | 4/2011 | Opsal et al. | |
| 8,253,940 B1* | 8/2012 | Green | G01J 3/0208 356/364 |
| 8,908,175 B1 | 12/2014 | Kandel et al. | |
| 9,518,916 B1* | 12/2016 | Pandev | G01N 21/255 |
| 2001/0033378 A1* | 10/2001 | Rosencwaig | G01B 11/0641 356/369 |
| 2004/0125373 A1* | 7/2004 | Oldenbourg | G02B 21/0092 356/364 |
| 2004/0218172 A1* | 11/2004 | DeVerse | G01J 3/2823 356/300 |
| 2005/0041250 A1* | 2/2005 | Opsal | G01B 11/0641 356/369 |
| 2006/0058682 A1* | 3/2006 | Miller | A61B 3/102 600/476 |
| 2006/0175528 A1* | 8/2006 | Greenaway | G01J 9/00 250/201.9 |
| 2009/0303571 A1* | 12/2009 | Sandstrom | G02B 5/1809 359/291 |
| 2010/0245819 A1* | 9/2010 | Li | G01B 11/0641 356/327 |
| 2011/0069312 A1 | 3/2011 | Kandel et al. | |
| 2013/0114085 A1* | 5/2013 | Wang | G01N 21/55 356/445 |
| 2013/0245985 A1* | 9/2013 | Flock | G03F 7/70625 702/105 |
| 2013/0321810 A1* | 12/2013 | Wang | G01N 21/211 356/369 |
| 2014/0111791 A1 | 4/2014 | Manassen et al. | |
| 2014/0132948 A1 | 5/2014 | Shchegrov | |
| 2014/0172394 A1 | 6/2014 | Kuznetsov et al. | |
| 2014/0222380 A1 | 8/2014 | Kuznetsov et al. | |
| 2014/0375981 A1 | 12/2014 | Wang et al. | |
| 2015/0058813 A1 | 2/2015 | Kim et al. | |

* cited by examiner

OPTICAL METROLOGY WITH SMALL ILLUMINATION SPOT SIZE

TECHNICAL FIELD

The described embodiments relate to metrology systems and methods, and more particularly to methods and systems for improved measurement resolution with smaller measurement box sizes.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

A lithographic process, as described above, is performed to selectively remove portions of a resist material overlaying the surface of a wafer, thereby exposing underlying areas of the specimen on which the resist is formed for selective processing such as etching, material deposition, implantation, and the like. Therefore, in many instances, the performance of the lithography process largely determines the characteristics (e.g., dimensions) of the structures formed on the specimen. Consequently, the trend in lithography is to design systems and components (e.g., resist materials) that are capable of forming patterns having ever smaller dimensions.

Inspection processes based on optical metrology are used at various steps during a semiconductor manufacturing process to detect defects on wafers to promote higher yield. Optical metrology techniques offer the potential for high throughput without the risk of sample destruction. A number of optical metrology based techniques including scatterometry implementations and associated analysis algorithms to characterize device geometry have been described. However, it remains a challenge to preserve a small measurement box size. A small measurement box size is especially important in semiconductor inline product metrology where the area available for metrology targets is minimal. The measurement box size refers to the minimum area on the specimen where measurement results are stable and not affected by edge effects (e.g., due to optical diffraction wings) in optical metrology. Hence, the smaller the measurement box size, the smaller the area required for metrology targets. In the semiconductor industry, where wafer space allocated to metrology targets is limited (often, within the scribe line or even within die), the desired box size specification can be often very challenging, such as 30 µm×30 µm, 10 µm×10 µm, or even smaller.

Diffraction, aberration, image quality, and other limiting effects must be controlled to achieve a smaller illumination spot size. In one example, a reflective optics ellipsometer allows for a smaller spot size on the metrology target by reducing chromatic aberrations commonly associated with the use of refractive elements. Such a system is described by U.S. Pat. No. 5,608,526 entitled "Focused beam spectroscopic ellipsometry method and system," issued Mar. 4, 1997, to KLA-Tencor Corporation, the contents of which are incorporated by reference as if fully set forth herein. In another example, a metrology tool employing an apodizing element is described by U.S. Pat. No. 5,859,424 entitled "Apodizing filter system useful for reducing spot size in optical measurements and other applications," issued Jan. 12, 1999, to KLA-Tencor Corporation, the contents of which are incorporated by reference as if fully set forth herein. The apodizer provides a smoothly varying spatial filter to reduce diffraction tails in the illumination spot on the sample.

In general, it is often desirable to configure metrology systems with multiple angles of incidence and several wavelength bands in an attempt to achieve small measurement spot size. For example, metrology systems having multiple angles of incidence are described by U.S. Pat. No. 6,429,943 entitled "Critical dimension analysis with simultaneous multiple angle of incidence measurements," issued Aug. 6, 2002, to KLA-Tencor Corporation, the contents of which are incorporated by reference as if fully set forth herein. In another example, metrology systems having several wavelength bands are described by U.S. Pat. No. 7,061,614 entitled "Measurement system with separate optimized beam paths," issued Jun. 13, 2006, to KLA-Tencor Corporation, the contents of which are incorporated by reference as if fully set forth herein. However, in some examples, e.g., in composition measurements where it is desirable to perform measurements at oblique, near-Brewster angles of incidence (AOI), geometric scaling effects cause an undesirable enlargement of the measurement box size at large AOIs.

To shrink the size of the measurement box size the amount of signal information that arises from the area surrounding the measurement target and reaches the detector must be minimized. To minimize undesirable signal contamination, the illumination light must be projected onto the measurement target with a minimum of spillover outside of the measurement target area.

In the past, the illumination spot size was reduced by increasing the system NA and reducing the size of the illumination aperture (e.g., a polarizer slit). Although increasing the NA addresses diffraction induced spillover, increasing the NA increases aberrations, increases cost, creates optical alignment difficulties, and reduces the transmission efficiency of the optical system. Although reducing the size of the illumination aperture addresses geometrical properties of the spot image, the reduction in size of the illumination aperture increases coherence effects, reduces light throughput, and requires a tightening of optical system tolerances.

Despite existing approaches designed to control measurement box size, achieving a small measurement box size specification over the full measurement range is very challenging. This is especially the case at both large oblique angles of incidence (AOI), where the incident beam covers a larger area, and at longer wavelengths, where diffraction effects introduce significant limitations.

As lithographic and inspection systems are pressed to higher resolutions, measurement box size becomes a limiting factor in maintaining device yield. Thus, improved methods and systems for achieving a small measurement box size associated with a variety of metrology technologies are desired.

SUMMARY

Methods and systems for reducing the illumination spot size projected onto a measurement target and associated spillover onto area surrounding a measurement target are described herein.

In one aspect, a spatial light modulator (SLM) is located in the illumination path between the illumination light source and the measurement sample. In some embodiments, the SLM is located in an optical pupil plane of the measurement system. The SLM is configured to modulate amplitude, phase distribution, or both, across the path of the illumination light to reduce wavefront errors and shape the amplitude and phase distribution of the beam. In a further aspect, the spatial light modulator enables programmable configuration of the phase distribution across the illumination beam. This may be employed to correct aberrations or cancel contamination signals. By way of non-limiting example, any of a transmissive liquid crystal display (LCD) device, a reflective liquid crystal on silicon (LCOS) device, a pixelated mirror device, and a deformable mirror device having a continuous surface may be employed as a SLM in the illumination path of a metrology system.

In a further aspect, a computing system determines a desired state of the SLM to implement a desired amplitude correction, phase distribution correction, or both, based on simulations.

In another further aspect, a computing system determines a desired state of the SLM to implement a desired amplitude correction, phase distribution correction, or both, based on wavefront measurements in an optical path of the metrology system.

In some embodiments, a wavefront sensor is located in a position along the optical path where the desired wavefront is known, i.e., the measured wavefront should be within a specified range of measured values. In these embodiments, a computing system compares the wavefront measurements provided by the wavefront sensor with the desired wavefront to determine the desired state of the SLM. Based on this feedback control approach, wavefront errors induced in the optical path before the wavefront measurement location are corrected.

Locating the wavefront sensor as close to the specimen as possible allows for correction of measured wavefront errors induced by the illumination optics directly. However, wavefront errors induced by the specimen itself and the collection optics are not visible in the wavefront measurement when the wavefront sensor is located in the illumination path.

In another further aspect, the wavefront sensor is located in the collection path, or the measurement detector itself is used to provide measurement feedback to determine the desired state of the SLM. For example, the measurement detector of the metrology system may be employed to measure the spot size quality on the wafer directly. In these embodiments, a defined metrology target (e.g., a 10×10 μm grid area surrounded by no grid) is measured and spectral data generated by the detector is evaluated by a computing system and compared with a desired spectral response. The computing system 130 determines corrections to the state of SLM to reduce the differences between the measured spectral data and the desired spectral data. In another example, the wavefront sensor can be located anywhere in the collection path. Wavefront measurements are performed using a defined metrology target as described hereinbefore. Corrections to the state of SLM are determined based on the difference between the measured wavefront and a desired wavefront at the point of wavefront measurement. In this manner, the state of SLM is adjusted to achieve a specific desired wavefront.

In another further aspect, the desired state of the SLM is determined based on both measurements and simulation data. For example, if the wavefront sensor is located in the optical path before a portion of the optical system for which correction is desired, the wavefront at the desired location is estimated based on a combination of the measured wavefront data and simulation data. Corrections to the state of the SLM are determined based on the estimated wavefront at the desired location and the desired wavefront at that location.

In some embodiments, the measurement and correction of the state of the SLM is performed iteratively until the measured wavefront matches the known desired wavefront. In some embodiments, the desired wavefront is selected to match wavefronts between a fleet of metrology systems.

In some embodiments, the wavefront sensor is located in a position along the optical path where the wavefront sensor provides wavefront measurement data as part of normal system operation. In some other embodiments, the wavefront sensor is located in a position where the wavefront sensor provides wavefront measurement data as part of a periodic maintenance operation.

In another aspect, a metrology system includes an illumination aperture having an image plane that is tilted at an oblique angle with respect to the beam of illumination light to overcome defocusing effects that arise in metrology systems that employ oblique illumination of the measurement sample.

In some embodiments, the illumination aperture is oriented such that the image plane of the illumination aperture, the principal plane of the objective lens, and the surface plane of the specimen under measurement intersect along a common line. This configuration satisfies the Scheimpflug condition and under this condition the illumination aperture is imaged onto the surface of specimen without blur.

In general, a variety of metrology system architectures benefit from a reduced measurement box size enabled by a spatial light modulator located in an illumination path, an illumination aperture having an image plane oriented at an oblique angle with respect to the illumination beam, or a combination of both.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for tailoring the illumination provided to a specimen in specific measurement applications are described herein. The illumination may be tailored to reduce the illumination spot size projected onto a measurement target and associated spillover onto area surrounding a measurement target. In another example, the illumination may be tailored to simplify optical design and alignment procedures. In yet another example, the illumination may be tailored to compensate for tool to tool variation. In some examples, a small illumination spot size may enable the use of a broad range of wavelengths and angles of incidence without having to expand the size of the measurement box. A smaller measurement box enables smaller metrology target sizes in many applications, thus preserving valuable wafer area. In some examples, smaller metrology targets may be located within the scribe lines, within the device area, in-die, or on the device itself.

Figure 1:
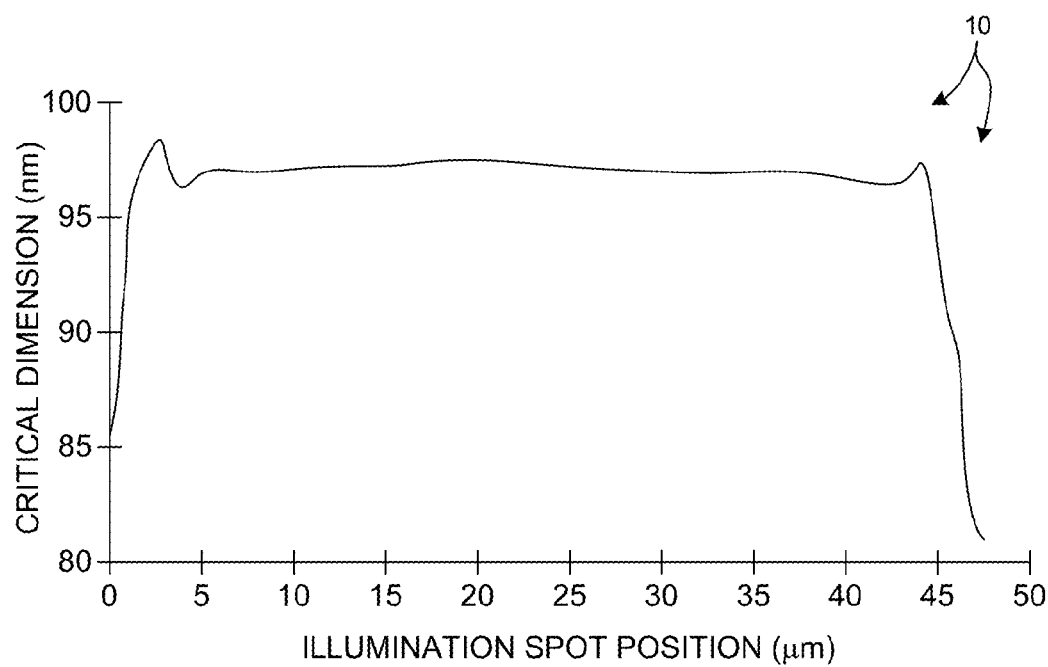
FIG. 1 is a plot 10 illustrative of reflectometer measurement results of a metrology target having a repeated device structure.

By way of example, FIG. 1 illustrates one way to characterize the measurement box size specification for a metrology tool. FIG. 1 is a plot 10 illustrative of reflectometer measurement results of a metrology target having a repeated device structure with a known 50 micrometer by 50 micrometer patterned area. The illumination spot size was scanned across the target. In the example provided, a critical dimension (CD) characterizing the target was measured by identifying a set of target parameters that gave the best fit to measured spectroscopic reflectometer signals. The CD variation is expected to stay within a prescribed range within this test target. Hence, it is presumed that an undesireable interaction of the illumination beam with the edges of the target area is occurring when the measurement results move outside of this range. In the illustrated example, the measurement is stable over a linear scan of approximately 38 micrometers. Therefore, the measurement box size associated with the measurement of the target by the reflectometer along the scan direction (e.g., x-direction) is 12 micrometers (i.e., the difference between the target length in the x-direction, 50 micrometers, and the portion of the target length along the x-direction that was reliably measured, 38 micrometers). In other words, the measurement of a metrology target with a patterned area less than 12 micrometers along the scan direction will not yield useful results due to the interaction of the illumination beam with the edges of the target area. Hence, the minimum measurement box size in this example is 12 micrometers in the x-direction. Note that the measurement box size along the orthogonal direction (e.g., y-direction) may be different and can depend on both the illumination beam properties and the target properties. Note that the use of a reflectometer is provided by way of non-limiting example as other measurement instruments (e.g., ellipsometers, scatterometers, etc.) may also be contemplated. Moreover, the characterization of the impact of target edge on the measurement of the target based on a critical dimension measurement is also provided by way of non-limiting example. Other metrics (e.g., feature height, sidewall angle, film thickness, refraction indices, composition, overlay, pitchwalk, goodness of fit, $\chi^2$, etc.) may also be contemplated.

The illumination spot size (i.e., spot size of the illumination light incident on the sample) is typically determined by a combination of geometrical image quality, diffraction effects, and aberration. In one example, geometric scaling effects impact the measurement box size. Oblique angles of incidence (AOI), although desirable for measurement techniques as such as ellipsometry, contribute to the enlargement of the illumination spot size. The illumination spot size is proportional to 1/cos(AOI), where AOI is measured from an axis normal to the surface under measurement. Hence, as the AOI increases, the projection of the illumination beam onto the surface under inspection grows. For example, an illumination beam producing a 20 μm geometric spot size at normal incidence (AOI=zero degrees) would produce a geometric spot size of approximately 28 micrometers at an AOI of 45 degrees, and a geometric spot size of approximately 58 micrometers at an AOI of 70 degrees. Hence, shorter wavelength illumination light that can be focused to a smaller effective spot size may still meet a small measurement box size specification at larger AOIs, where longer wavelength illumination light may not.

Figure 2:
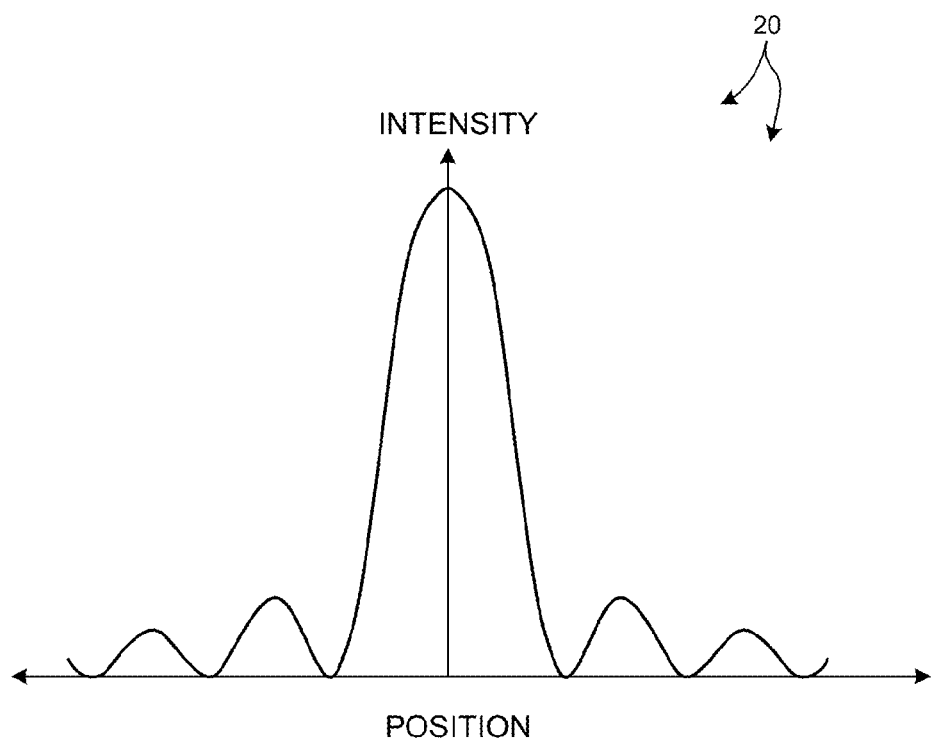
FIG. 2 illustrates a plot 20 of an exemplary intensity distribution of an illumination spot.

In another example, diffractive effects impact measurement box size. It is known that when trying to focus a beam of light onto a small spot, a central bright spot is accompanied by diffraction tails. FIG. 2 illustrates a plot 20 of an exemplary intensity distribution of an illumination spot over the area of incidence of the sample. As illustrated in FIG. 2, the intensity peaks at a central illumination spot, but rather than tapering off to zero away from the center of the beam, the intensity ripples away from the center due to diffraction effects, thus increasing the effective spot size. The effective spot size, as limited by diffraction, scales with the wavelength of the illumination light. Thus, shorter wavelength illumination light can be focused to a smaller effective spot size.

In yet another example, optical aberration effects impact measurement box size. The impact of some optical aberration effects also depends on the illumination wavelength. Hence, selection of a particular subset of wavelengths of illumination light can be used to mitigate the effect of optical aberration on measurement box size. In addition, optical aberration is also defined by the details of the optical design. Thus, the selection of a particular subset of wavelengths of illumination light to reduce the impact of optical aberration also depends on the particular optical design.

Figure 3:
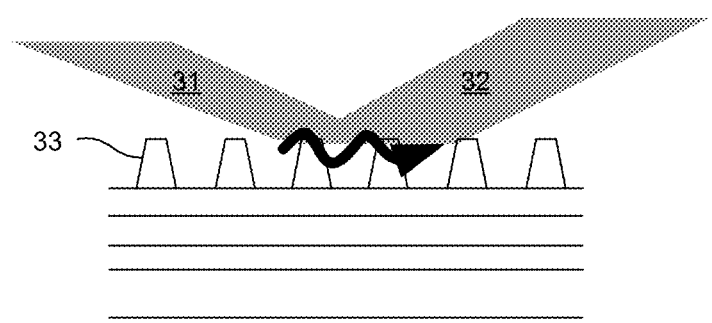
FIG. 3 is a diagram illustrative of an incident beam 31 interacting with a target 33.

In yet another example, the interaction between the illumination light and the target structure itself impacts effective measurement box size. An often overlooked limitation on the effective measurement box size is due to the interaction of the incident beam with the sample. For example, as illustrated in FIG. 3, an incident beam 31 interacts with a target 33 (e.g. a grating target commonly used in CD metrology). The interaction can excite eigenmodes of the structure such as waveguide modes, surface plasmon polaritons, or result in other types of resonant or non-resonant interaction with the target that extend the effective interaction area beyond the illuminated spot size. As illustrated schematically in FIG. 3, this would result in the collection side of the metrology tool detecting an outgoing beam 32 coming from a larger area than the illuminated spot size. This increases the metrology box size compared to the idealistic case when the effect of interaction with the sample is ignored (i.e., when a perfectly reflecting mirror surface is assumed).

Figure 4:
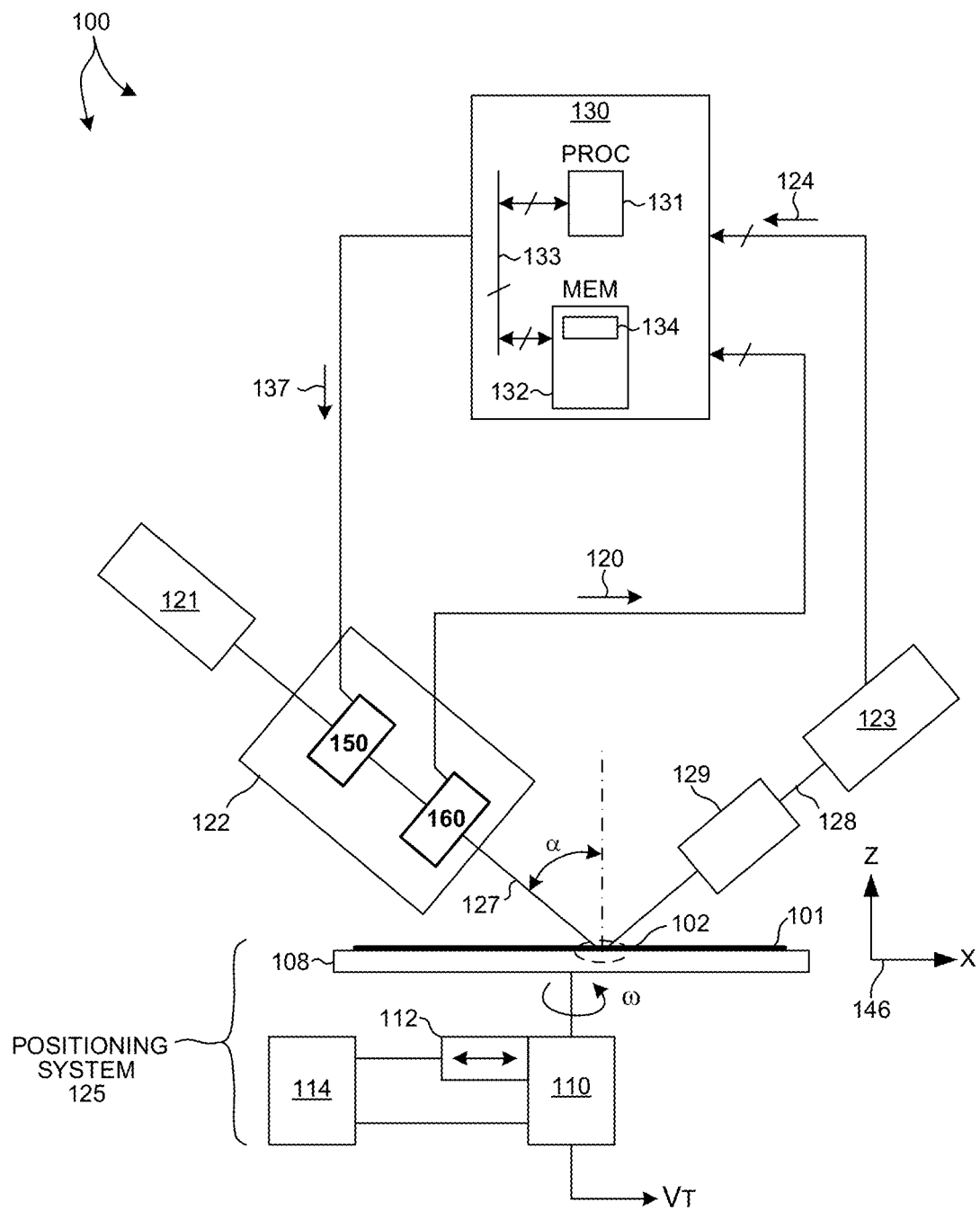
FIG. 4 illustrates a metrology tool 100 for measuring characteristics of a specimen within a small measurement box size.

FIG. 4 illustrates an embodiment of a metrology tool 100 for measuring characteristics of a specimen within a small measurement box size. In one aspect, limitations caused by any of geometric effects, light diffraction effects, aberration effects, and interactions between illumination light and the target are overcome by including a spatial light modulator (SLM) in the illumination path between the illumination light source and the measurement sample. The SLM is configured to modulate amplitude, phase distribution, or both, across the path of the illumination light to reduce wavefront errors. If uncorrected these wavefront errors would manifest themselves at the detector. With wavefront correction, a smaller measurement box size is achieved than would otherwise be possible if the wavefront errors were left uncorrected.

As depicted in FIG. 4, metrology system 100 may be used to perform optical scatterometry measurements over a measurement box area 102 of a specimen 101 disposed on a specimen positioning system 125. In some embodiments, the measurement box size is thirty micrometers or less in any direction. In some embodiments, the measurement box size is ten micrometers or less in any direction.

In general, and as depicted in FIG. 4, metrology tool 100 includes an optical illumination source 121 and an illumination optics subsystem 122 that is configured to shape and direct incident optical illumination beam 127 from optical illumination source 121 to the measurement box area 102 of specimen 101. By way of non-limiting example, optical illumination source 121 includes one or more arc lamps, lasers, light emitting diodes, laser driven plasma sources, and laser driven supercontinuum sources, or any combination thereof. In general, any suitable optical illumination source or combination of sources may be contemplated. In some embodiments, optical illumination source 121 is configured to generate illumination light having wavelength components between 100 nanometers and 2500 nanometers.

The illumination optics subsystem 122 is configured to collimate or focus incident optical illumination beam 127 to measurement box area 102 of specimen 101. In some examples, illumination optics 122 is configured to monochromatize incident optical illumination beam 127. In some embodiments, illumination optics 122 includes one or more optical mirrors, focusing or defocusing optics (reflective or refractive), optical polarization components including polarizers and waveplates, optical apertures, optical monochromators, and optical beam stops, or any combination thereof.

Collection optics 129 collect an amount of collected light 128 scattered, reflected, diffracted or refracted from specimen 101 and direct the collected light 128 to detector 123. Detector 123 generates an output signal 124 indicative of a response of the specimen to the incident illumination light.

In some embodiments, scattered optical radiation 128 is detected by optical detector 123 while specimen positioning system 125 locates and orients specimen 101 to produce angularly resolved scattered optical radiation. The optical detector 123 is able to resolve one or more optical photon energies and produces signals for each optical energy component indicative of properties of the specimen. In some embodiments, the optical detector 123 is any of a CCD array, a photodiode array, a CMOS detector or a photomultiplier tube. In some embodiments, optical detector 123 is a spectrometer and measurement data 124 includes an indication of the measured spectral response of the specimen based on one or more sampling processes implemented by an optical spectrometer.

Metrology tool 100 also includes a computing system 130 employed to acquire signals 124 generated by optical detector 123 and determine properties of the specimen based at least in part on the acquired signals. In a some embodiments, computing system 130 is configured to access model parameters in real-time, employing Real Time Critical Dimensioning (RTCD), or it may access libraries of pre-computed models for determining a value of at least one specimen parameter value associated with the specimen 101. In general, some form of CD-engine may be used to evaluate the difference between assigned CD parameters of a specimen and CD parameters associated with the measured specimen. Exemplary methods and systems for computing specimen parameter values are described in U.S. Pat. No. 7,826,071, issued on Nov. 2, 2010, to KLA-Tencor Corp., the entirety of which is incorporated herein by reference. In general, measurement models associated with not just CD, but also thin film, overlay, pitchwalk, focus/dose, and composition measurements may be applied by computing system 130 to resolve specimen parameter values, by way of non-limiting example. In some other embodiments, computing system 130 is configured to determine properties of the specimen without reference to a physically based reference model, e.g., signal response model based measurements or overlay measurements.

As illustrated in FIG. 4, metrology tool 100 includes a specimen positioning system 125 configured to move specimen 101 under illumination beam 127. In some embodiments, computing system 130 communicates command signals to motion controller 114 of specimen positioning system 125 that indicate the desired position of specimen 101. In response, motion controller 125 generates command signals to the various actuators of specimen positioning system 125 to achieve the desired positioning of specimen 101.

In the embodiment depicted in FIG. 4, specimen positioning system 125 includes a wafer chuck 108, motion controller 114, a rotation stage 110 and a translation stage 112, and a z-stage (not shown). Rotation stage 110 and translation stage 112 are configured to translate specimen 101 in two dimensions within the x-y plane depicted by coordinate system 146. The z-stage is configured to translate specimen 101 in the z-direction depicted by coordinate system 146. Specimen 101 is supported on wafer chuck 108. In some embodiments, specimen 101 is located with its geometric center approximately aligned the axis of rotation of rotation stage 110. In this manner, rotation stage 110 spins specimen 101 about its geometric center at a specified angular velocity, w, within an acceptable tolerance. In addition, translation stage 112 translates the specimen 101 in a direction approximately perpendicular to the axis of rotation of rotation stage 110 at a specified velocity, $V_T$. Motion controller 114 coordinates the spinning of specimen 101 by rotation stage 110 and the translation of specimen 101 by translation stage 112 to achieve the desired scanning motion of specimen 101 within system 100.

In one aspect, the illumination optics subsystem 122 includes SLM 150 in the illumination path between the illumination light source and the measurement sample. SLM 150 is configured to modulate amplitude, phase, or both, across the path of the illumination light to reduce wavefront errors (e.g., aberrations).

In a further aspect, the spatial light modulator enables programmable configuration of the phase distribution across the illumination beam. This may be employed to correct aberrations or cancel contamination signals. In some examples, the desired phase characteristics are determined based at least in part on the specific metrology target. In this manner, the illumination provided by the metrology system is specifically tuned to a specific target. This tuning can be performed during measurement, as part of a measurement recipe set-up, or as a part of the periodic maintenance of the metrology tool.

A number of different types of SLMs may be employed by metrology system 100 to affect the phase of the illumination light. By way of non-limiting example, any of a transmissive liquid crystal display (LCD) device, a reflective liquid crystal on silicon (LCOS) device, a pixelated mirror device, and a deformable mirror device having a continuous surface may be employed as a SLM in the illumination path of metrology system 100. In general, any device suitable to spatially control the phase of the illumination light of metrology system 100 may be contemplated.

In a preferred embodiment SLM 150 is a deformable mirror (DM) device based on an actuated continuous reflective surface. A continuous mirror surface has a 100%, or close to 100% fill factor, thus light losses are limited compared to a pixelated (i.e., segmented) mirror device. The deformation of a portion of the continuous reflective surface introduces an optical path difference (OPD) over a portion of the illumination beam. For an achromatic design, the OPD introduces a wavefront distortion that is the same for all wavelengths. This enables the use of a broad range of wavelengths with a single shape of the DM. An actuated, continuous surface assures that programmed shapes are smooth, and that complex shapes may be achieved with a minimum number of actuators due to the inherent interpolation between actuators provided by the continuous reflective membrane surface. Compared to a pixelated surface, the spatial resolution across an actuated, continuous, reflective surface is not limited to the number of actuators. Moreover, there is no parasitic diffraction induced as is the case at the edges of each mirror pixel of a segmented mirror surface. In one non-limiting example, a suitable continuous DM device is manufactured by Boston Micromachines Corporation, Cambridge, Mass. (USA). Such a continuous DM device has a fast response rate (e.g., many kHz or more) with a large range of deformations (e.g., stroke of 1.5 µm-5.5 µm or more) that enables the rapid correction of high level aberrations.

As described hereinbefore, a SLM such as a deformable mirror may be located anywhere in the illumination path from the illumination source 121 to the specimen 101. The shape and total required stroke of a DM are determined by the chosen location. For aberration correction, a preferred location for a DM is in a plane conjugate to a pupil plane of the optical system. In this manner, the angular distribution of the incident beams is expected to be minimal and only aberrations need to be addressed. A DM placed at or near a pupil plane conjugate location does not correct field dependent aberrations. However, it is possible to correct the aberrations at the edges of the field at the expense of increasing center field aberrations. This will reduce the size of the effective edge of field spot while increasing the size of the effective center field spot. In general, the highest level aberrations are located at the edges of the field. Thus, overall, the DM is effective at reducing the 'tails' of the illumination intensity distribution of the illumination spot by correcting aberrations at the edges of the field.

In systems designed with no pupil plane or with a pupil plane that is not readily accessible, it is preferable to locate the DM along the illumination path where beam divergence is minimal.

Figure 5:
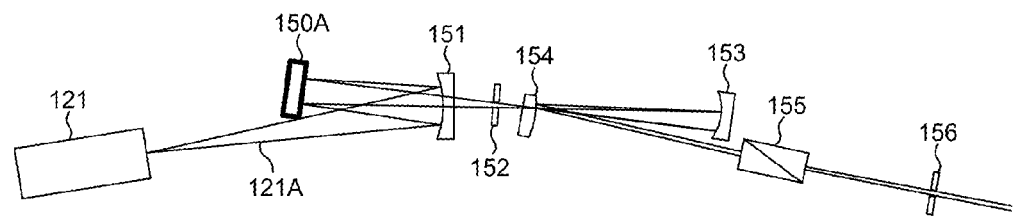
FIG. 5 depicts an illumination source 121 and a portion of an illumination optics subsystem that includes a deformable mirror in one embodiment.

FIG. 5 depicts an illumination source 121 and a portion of an illumination optics subsystem that includes a DM in one embodiment. In the depicted embodiment, a DM 150A is located in the illumination path before a polarizer slit 156 of the illumination optics subsystem. An illumination source 121 generates a diverging beam of illumination light that is directed to a mirror 151. After reflection from mirror 151, the beam of illumination light is approximately collimated and is directed toward DM 150A. Upon reflection from the surface of DM 150A, the beam of illumination light is modulated across the field in amplitude, phase, or both amplitude and phase by the shape of the surface of DM 150A. The modulated beam of illumination light passes through a filter 152, and reflects from mirror 153, then mirror 154 before passing through polarizer 155 (e.g., Rochon prism), and finally through polarizer slit 156.

Figure 6:
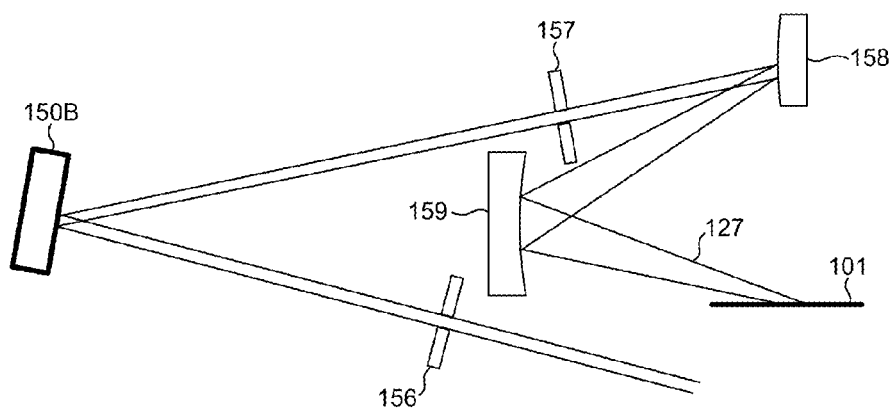
FIG. 6 depicts an illumination source 121 and a portion of an illumination optics subsystem that includes a deformable mirror in another embodiment.

FIG. 6 depicts an illumination source 121 and a portion of an illumination optics subsystem that includes a DM in another embodiment. In the depicted embodiment, a DM 150B is located in the illumination path after a polarizer slit 156 of the illumination optics subsystem. A beam of illumination light passes through polarizer slit 156 and is directed toward DM 150B. Upon reflection from the surface of DM 150B, the beam of illumination light is modulated across the field in amplitude, phase, or both amplitude and phase by the shape of the surface of DM 150B. The modulated beam of illumination light passes through an apodizer 157, and reflects from mirror 158, then mirror 159 before incidence on the surface of specimen 101. In some embodiments, the surface of the DM is treated such that the reflectivity varies as a function of location across the surface of the DM. In these embodiments, the amplitude of the beam of illumination light is modulated across the field based on the spatially varying reflectivity of the DM. In some examples, the mirror coatings spatially vary in geometry, composition, or both, to achieve a desired reflectivity profile across the surface of the DM.

Figure 26:
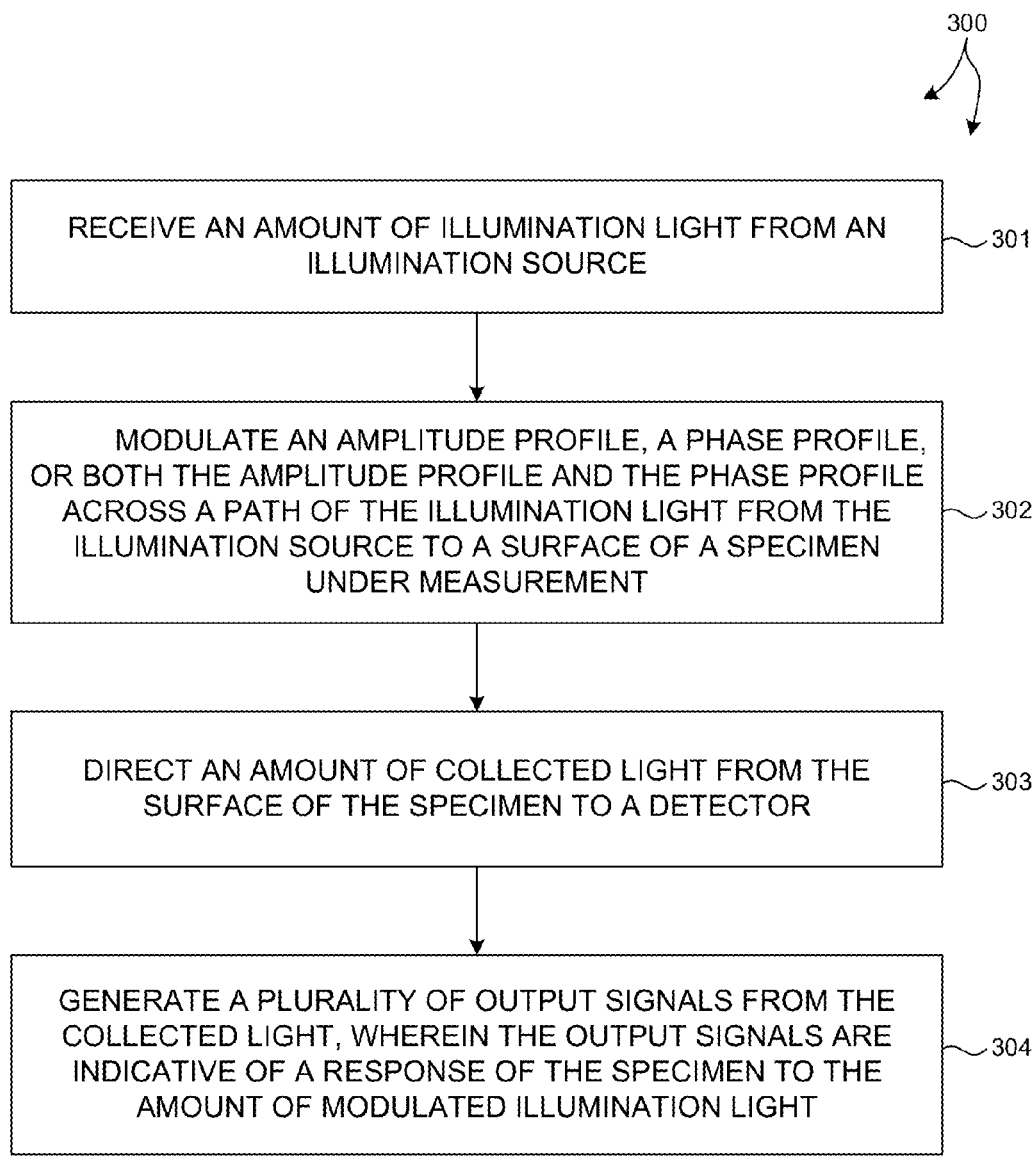
FIG. 26 illustrates a flowchart illustrative of a method 300 of modulating the illumination light of a metrology system to reduce measurement box size.

FIG. 26 illustrates a method 300 suitable for implementation by a metrology system (e.g., metrology system 100 illustrated in FIG. 4). In one aspect, it is recognized that data processing blocks of method 300 may be carried out via a pre-programmed algorithm executed by one or more processors of computing system 130. While the following description of the method 300 is presented in the context of metrology system 100, it is recognized herein that the particular structural aspects of metrology system 100 do not represent limitations and should be interpreted as illustrative only.

In block 301, a SLM located in the illumination path of a metrology system receives an amount of illumination light from an illumination source.

In block 302, the SLM modulates an amplitude profile, a phase profile, or both the amplitude profile and the phase profile across a path of the illumination light from the illumination source to a surface of a specimen under measurement.

In block 303, an amount of collected light from the surface of the specimen is directed to a detector, for example, by collection optics.

In block 304, a plurality of output signals are generated from the collected light by the detector. The output signals are indicative of a response of the specimen to the amount of modulated illumination light.

In a further aspect, a computing system (e.g., computing system 130) determines a desired state of the SLM (e.g., shape of DM) to implement a desired amplitude correction, phase distribution correction, or both, based on simulations. For example, the shape of the surface of a deformable mirror such as DM 150A and 150B is programmable and the desired shape is determined based on simulations of the system (i.e., simulations and calculations based on a model of the system). For example, a phase mask is simulated at the location of the deformable mirror to simulate overall system performance with the DM in place. The shape of the DM is calculated to achieve the desired result (e.g., reduced spot size). The system model includes all system design metrics (e.g., coatings, manufacturing errors, etc.). For example, in general, the effects of oblique angle of incidence, diffraction, aberrations, and interaction between illumination light and the target can be rigorously calculated with a proper electromagnetic simulation engine. By way of non-limiting examples, such calculations can be performed using the finite-element method, RCWA, finite difference time domain analysis (FDTD), beam propagation method (BPM), and geometrical and physical optics simulations. Alternatively, other approaches may also be contemplated. In this manner, determination of the desired state of the SLM to achieve small measurement box size is achieved based on a model of the effects of finite spot illumination, propagation of light through optical elements, etc.

In another further aspect, a computing system (e.g., computing system 130) communicates control signals (e.g., signals 137 depicted in FIG. 4) to cause the programmable SLM 150 to implement the desired state. For example, control signals 137 cause a DM to implement a desired surface shape determined by computing system 130. In some embodiments, the surface shape of the DM is carefully calibrated to achieve the desired phase distribution across the mirror. In addition, the DM is precisely located in both position and orientation within the optical system. In some examples, the computing system communicates control signals that cause programmable SLM 150 to take on a special shape useful for registration and alignment of the optical system. In one example, the SLM 150 may take on a V-shape to facilitate alignment in a particular direction (e.g., x-direction). These special shapes are different from the shapes implemented by SLM 150 during measurement operations.

In another further aspect, a computing system (e.g., computing system 130) determines a desired state of the SLM (e.g., shape of DM) to implement a desired amplitude correction, phase distribution correction, or both, based on wavefront measurements in an optical path of the metrology system. For example, the desired shape of the surface of a deformable mirror such as DM 150A and 150B is determined based on measurements of the illumination light by a wavefront sensor located in an optical path between the illumination source and the measurement system detector. In the embodiment depicted in FIG. 4, wavefront sensor 160 is disposed in the illumination path between SLM 150 and specimen 101. However, in general, wavefront sensor 160 may be disposed anywhere in the optical path between illumination source 121 and detector 123.

In some embodiments, a wavefront sensor is located in a position along the optical path where the desired wavefront is known. In these embodiments, a computing system compares the wavefront measurements provided by the wavefront sensor with the desired wavefront to determine the desired state of the SLM. Based on this feedback control approach, wavefront errors induced in the optical path before the wavefront measurement location are corrected. In this manner, the errors induced by the optical system before the point of wavefront measurement are observable in the wavefront measurement. The errors can be identified based on differences between the measured wavefront and the desired wavefront and corrected in a closed loop or semi-closed loop manner.

As depicted in FIG. 4, a wavefront is measured by wavefront sensor 160 (e.g., interferometer, Hartmann-Shack sensor, etc.). An indication 120 of the measured wavefront is communicated to computing system 130. Computing system 130 determines the desired shape of the DM. A command signal 137 is communicated from computing system 130 to DM 150 to adjust the shape of the deformable mirror to realize the desired shape. In some embodiments, the measurement and correction of the mirror shape is performed iteratively until the measured wavefront matches the known desired wavefront.

In some embodiments, the desired wavefront is selected to match wavefronts across one or more metrology systems. Tool-to-tool matching and measurement consistency over time and over different measurement applications are improved by matching wavefronts across one or more metrology systems. More specifically, the shape of the deformable mirror is optimized such that differences between measured wavefronts generated by a reference system and a target system are minimized for measurements of the same metrology targets. The updated mirror shape is employed in subsequent measurement analyses performed by the target metrology system (e.g., CD measurements, shape measurements, thin-film measurements, CD matching applications, pitchwalk measurements, overlay measurements, composition measurements, focus/dose measurements, etc.).

The terms reference metrology system and target metrology system generally refer to a metrology system status (i.e., target) that requires adaptation of the SLM to obtain measurement consistency with another metrology system status (i.e., reference). In this manner, the target is being calibrated with respect to the reference.

In some examples, the target metrology system and the reference metrology system are different tools. For example, in a manufacturing context, it may be advantageous to have a fleet of metrology systems each calibrated to a single reference metrology system. In this manner, each of the fleet of metrology systems is consistent with a single reference tool. In another example, it may be advantageous to have a one or more metrology systems each calibrated to a fleet average of many metrology systems. In this manner, each of the metrology systems is consistent with an entire fleet of metrology tools. In another example, reference and target systems are the same system measured at different times (e.g., before and after a hardware maintenance operation).

Figure 7:
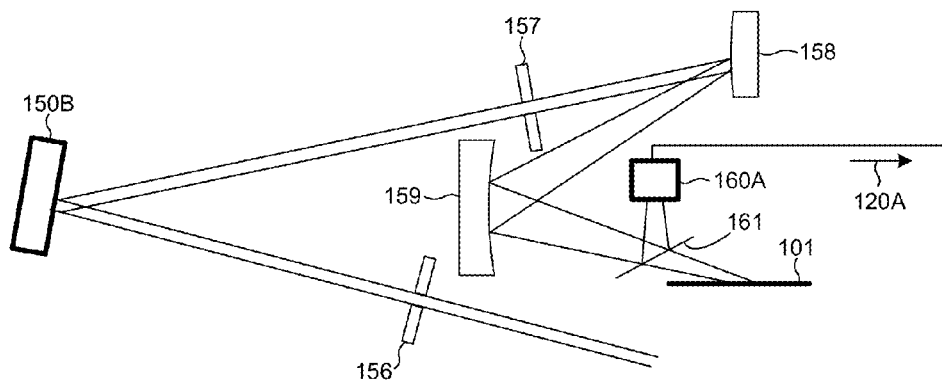
FIG. 7 depicts a portion of an illumination optics subsystem including a wavefront sensor 160A located in the illumination optical path after SLM 150, but before specimen 101.

In some embodiments, the wavefront sensor is located in a position along the optical path where the wavefront sensor provides wavefront measurement data as part of normal online system operation. FIG. 7 depicts a portion of an illumination optics subsystem including a wavefront sensor 160A located in the illumination optical path after SLM 150, but before specimen 101. FIG. 7 includes like numbered elements as described with reference to FIG. 6. A beam of illumination light passes through polarizer slit 156 and is directed toward DM 150B. Upon reflection from the surface of DM 150B, the beam of illumination light is modulated across the field in amplitude, phase, or both amplitude and phase by the shape of the surface of DM 150B. The modulated beam of illumination light passes through an apodizer 157, reflects from mirror 158, then mirror 159 before reaching beam splitter 161. A portion of the modulated beam of illumination light passes through beam splitter and is incident on the surface of specimen 101. Another portion of the modulated beam of illumination light is directed toward wavefront sensor 160A by beam splitter 161. Wavefront sensor 160A generates an output signal 120A indicative of the wavefront of the illumination light at the measured location.

Figure 8:
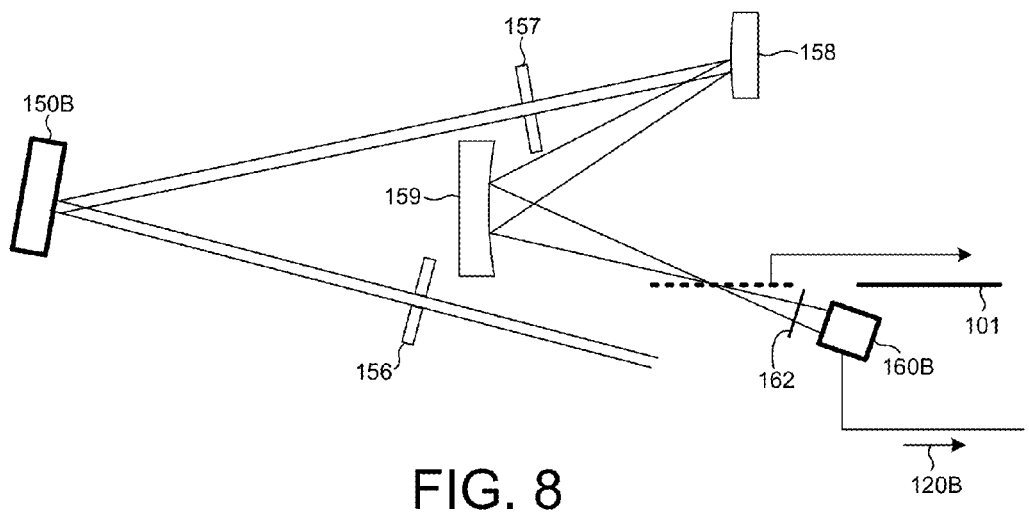
FIG. 8 depicts a portion of an illumination optics subsystem including a wavefront sensor 160B located in a periodic maintenance location after SLM 150.

In some other embodiments, the wavefront sensor is located in a position where the wavefront sensor provides wavefront measurement data as part of a periodic maintenance operation. FIG. 8 depicts a portion of an illumination optics subsystem including a wavefront sensor 160B located in a periodic maintenance location after SLM 150. FIG. 8 includes like numbered elements as described with reference to FIG. 6. A beam of illumination light passes through polarizer slit 156 and is directed toward DM 150B. Upon reflection from the surface of DM 150B, the beam of illumination light is modulated across the field in amplitude, phase, or both amplitude and phase by the shape of the surface of DM 150B. The modulated beam of illumination light passes through an apodizer 157, reflects from mirror 158, then mirror 159, and passes through filter 162 before reaching wavefront sensor 160B. Wavefront sensor 160B generates an output signal 120B indicative of the wavefront of the illumination light at the measured location. As depicted in FIG. 8, during a periodic maintenance operation specimen 101 is out of the optical path of the illumination light and the wavefront sensor 160B is moved into the optical path of the illumination light.

As depicted in FIGS. 7 and 8, in some embodiments it is desireable to locate the wavefront sensor 160 close to the location where measurements of the specimen take place. In this manner, wavefront errors induced by the illumination optics can be measured and corrected as near the measurement location as possible. In some examples, wavefront errors before the specimen measurement location are corrected such that the illumination waveforms across a fleet of tools are nearly identical at the point of measurement of the specimen. In some examples, a phase error of less than 0.01 nanometers across a fleet of tools is obtained.

Locating the wavefront sensor as close to the specimen as possible allows for correction of measured wavefront errors induced by the illumination optics directly. However, wavefront errors induced by the specimen itself and the collection optics are not visible in the wavefront measurement when the wavefront sensor is located in the illumination path. In another further aspect, the wavefront sensor is located in the collection path, or the measurement detector itself is used to provide measurement feedback to determine the desired state of a SLM (e.g., shape of a DM). For example, detector 123 may be employed to measure the spot size quality on the wafer directly. In these embodiments, a defined metrology target (e.g., a 10×10 µm grid area surrounded by no grid) is measured and spectral data generated by the detector 123 is evaluated by computing system 130 and compared with a desired spectral response. Computing system 130 determines corrections to the state of SLM 150 to reduce the differences between the measured spectral data and the desired spectral data. In some embodiments, the desired spectral response could be the spectral response obtained by measuring a larger target (e.g., 20×20 μm grid area surrounded by no grid) which does not result in 'tails' outside the grid area. In this manner, a set of metrology targets of decreasing size could be used to iteratively arrive at desired state of SLM 150 that results in a small measurement box size.

In general, a wavefront sensor can be located anywhere in the collection path. Wavefront measurements are performed using a defined metrology target as described hereinbefore. Corrections to the state of SLM 150 are determined based on the difference between the measured wavefront and a desired wavefront at the point of wavefront measurement. In this manner, the state of SLM 150 is adjusted to achieve a specific desired wavefront.

As described hereinbefore, locating the wavefront sensor as close to the specimen as possible allows for correction of measured wavefront errors induced by the illumination optics directly. However, wavefront errors induced by the specimen itself and the collection optics are not visible in the wavefront measurement when the wavefront sensor is located in the illumination path. In a further aspect, the desired state of the SLM is determined based on both measurements and simulation data.

If the wavefront sensor is located in the optical path before a portion of the optical system for which correction is desired, the wavefront at the desired location is estimated based on a combination of the measured wavefront data and simulation data. Corrections to the state of the SLM are determined based on the estimated wavefront at the desired location and the desired wavefront at that location.

Although the embodiments described with reference to of FIGS. 5-8 refer to a deformable mirror specifically, in general, any programmable spatial light modulator may be utilized to achieve a desired wavefront in accordance with the methods described herein.

Figure 27:
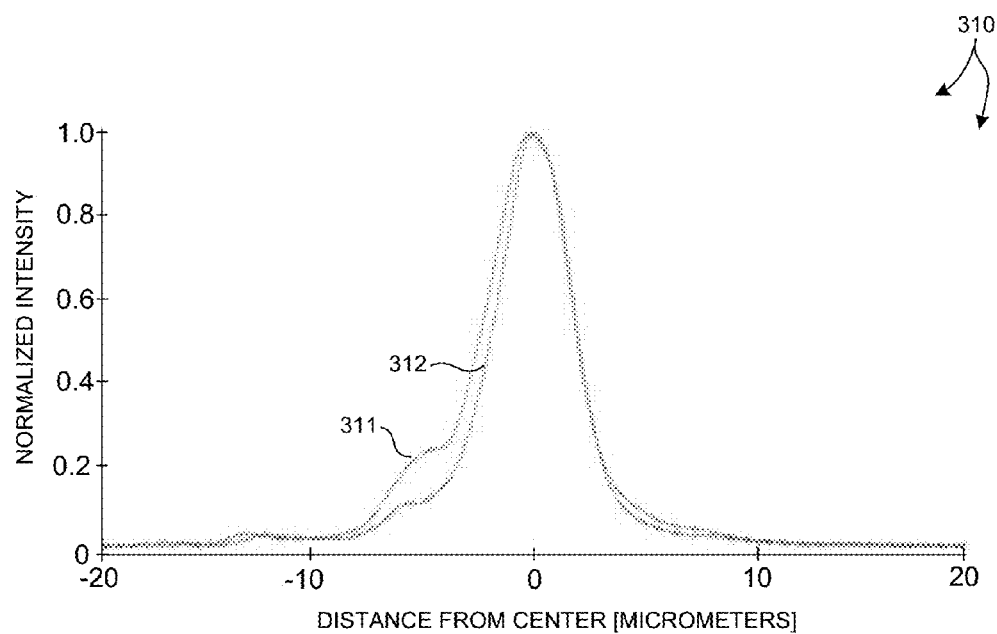
FIG. 27 illustrates a plot 310 illustrative of a measured reduction in illumination spot size due the use of a deformable mirror in one example.

FIG. 27 illustrates a plot 310 illustrative of a measured reduction in illumination spot size due the use of a deformable mirror as described herein. Plot 310 depicts the projection of illumination light from a laser based light source onto a specimen under measurement by illumination optics. Plotline 311 depicts the intensity distribution across the illumination beam at the point of incidence with a specimen under measurement when the illumination optics includes a planar mirror surface in the illumination optical beam path. Plotline 312 depicts the intensity distribution across the illumination beam at the point of incidence with a specimen under measurement when the illumination optics includes a deformed mirror surface in the illumination optical beam path. In this example, a 13% reduction in illumination spot size is achieved.

Figure 28:
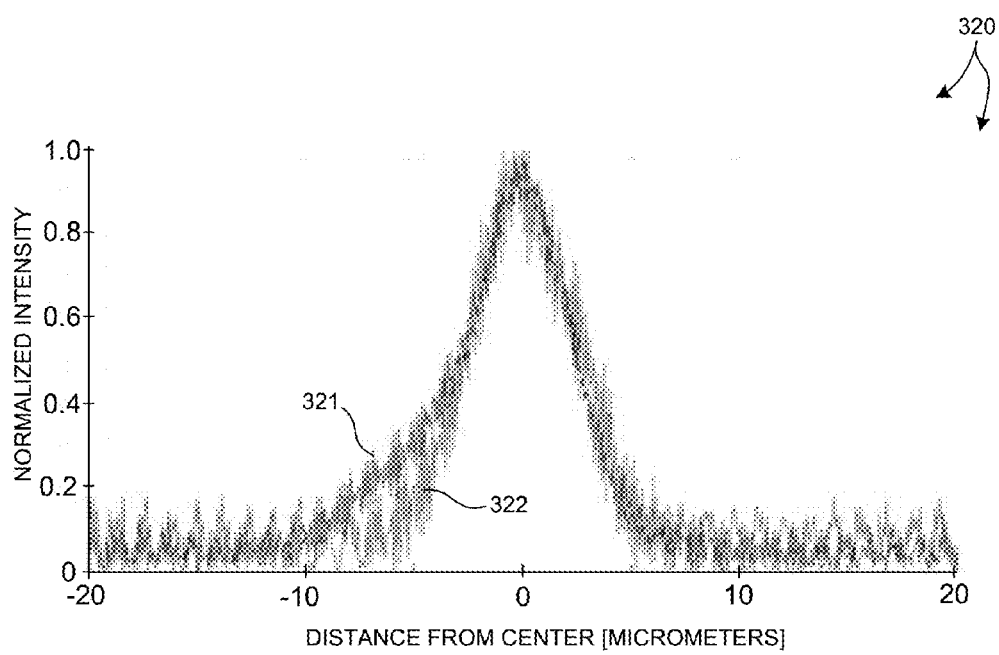
FIG. 28 illustrates a plot 320 illustrative of a measured reduction in illumination spot size due the use of a deformable mirror in another example.

FIG. 28 illustrates a plot 320 illustrative of a measured reduction in illumination spot size due the use of a deformable mirror as described herein. Plot 320 depicts the projection of illumination light from a laser driven light source (LDLS) onto a specimen under measurement by illumination optics. Plotline 321 depicts the intensity distribution across the illumination beam at the point of incidence with a specimen under measurement when the illumination optics includes a planar mirror surface in the illumination optical beam path. Plotline 322 depicts the intensity distribution across the illumination beam at the point of incidence with a specimen under measurement when the illumination optics includes a deformed mirror surface in the illumination optical beam path. In this example, a 15% reduction in illumination spot size is achieved.

A SLM may be used in a simple optical system, such as a system comprised of spherical optical elements to achieve a higher level of optical quality by correcting system aberrations. However, in general, a SLM may be used to implement an aspheric optical system without using complex and costly aspheric optical elements. Freeform aspheric surfaces are often difficult to manufacture and require precise alignment. A programmable SLM may be employed to mimic the optical response of an aspheric optical element without precise alignment by tuning the SLM in situ. Therefore, the use of a SLM in a metrology tool is not limited to reducing the spot size of the system. The SLM may also be employed to improve the overall optical quality of the system by reducing aberrations and replacing aspheric elements in a variety of metrology tools, e.g., spectroscopic ellipsometer or reflectometer systems, beam profile reflectometer/angle resolved scatterometer systems, spectroscopic scatterometer systems, single wavelength ellipsometer systems, and other systems.

It should be recognized that various steps described throughout the present disclosure may be carried out by a single computer system 130 or, alternatively, a multiple computer system 130. Moreover, different subsystems of the system 100, such as the specimen positioning system 125, may include a computer system suitable for carrying out at least a portion of the steps described herein. Therefore, the aforementioned description should not be interpreted as a limitation on the present invention but merely an illustration. Further, the one or more computing systems 130 may be configured to perform any other step(s) of any of the method embodiments described herein.

In addition, the computer system 130 may be communicatively coupled to the optical detector 123 and the SLM 150 in any manner known in the art. For example, the one or more computing systems 130 may be coupled to computing systems associated with the optical detector 123 and illumination optics subsystem 122. In another example, any of the optical detector 123 and the illumination optics subsystem 122 may be controlled directly by a single computer system coupled to computer system 130.

The computer system 130 may be configured to receive and/or acquire data or information from the subsystems of the system (e.g., optical detector 123, wavefront sensor 160, and the like) by a transmission medium that may include wireline and/or wireless portions. In this manner, the transmission medium may serve as a data link between the computer system 130 and other subsystems of the system 100.

Computer system 130 of the metrology system 100 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 130 and other systems (e.g., memory on-board metrology system 100, external memory, or external systems). For example, the computing system 130 may be configured to receive measurement data (e.g., signals 124) from a storage medium (i.e., memory 132 or an external memory) via a data link. In one example, spectral results obtained using a spectrometer of optical detector 123 may be stored in a permanent or semi-permanent memory device (e.g., memory 132 or an external memory). In another example, desired states of SLM 150 determined by computer system 130, or another computing system may be stored in a permanent or semi-permanent memory device (e.g., memory 132 or an external memory). In this regard, the desired states may be imported from on-board memory or from an external memory system. Moreover, the computer system 130 may send data to other systems via a transmission medium. For instance, desired states of SLM 150 determined by computer system 130, or another computing system may be stored in a permanent or semi-permanent memory device (e.g., memory 132 or an external memory). In this regard, results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 4, program instructions stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

Although, determining the desired state of the SLM 150 may be realized by computer system 130, it is contemplated that the desired state may be determined by other computer systems (e.g., a computer system external to metrology tool 100). For example, it is contemplated that the desired state of the SLM is determined prior to its use in a production environment. In these examples, it is contemplated that the determination of the desired shape of the SLM is realized by one or more external computer systems.

In another aspect, a metrology system includes an illumination aperture having an image plane that is tilted at an oblique angle with respect to the beam of illumination light to overcome defocusing effects that arise in metrology systems that employ oblique illumination of the measurement sample.

Figure 9:
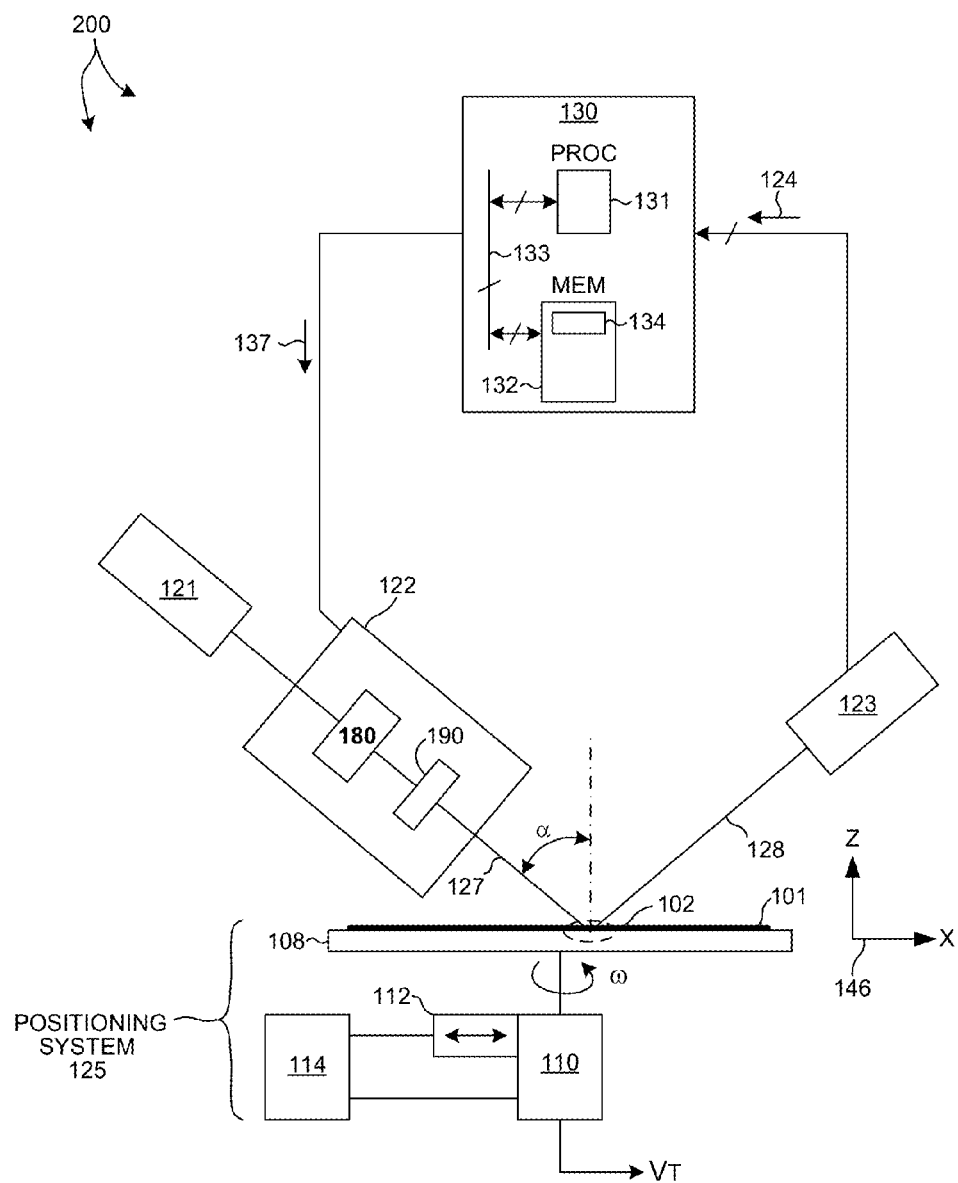
FIG. 9 illustrates a metrology tool 200 for measuring characteristics of a specimen within a small measurement box size in another embodiment.

FIG. 9 illustrates a metrology tool 200 for measuring characteristics of a specimen within a small measurement box size in another embodiment. As illustrated in FIG. 9, metrology system 200 includes similar, like numbered elements described with reference to FIG. 4. In one aspect, the illumination optics subsystem 122 includes an illumination aperture 180 having an image plane that is tilted at an oblique angle with respect to the beam of illumination light 127. Illumination aperture 180 is located at an intermediate image plane of both the illumination source 121 and a portion of the illumination optical subsystem 190 (e.g., the objective).

Figure 10:
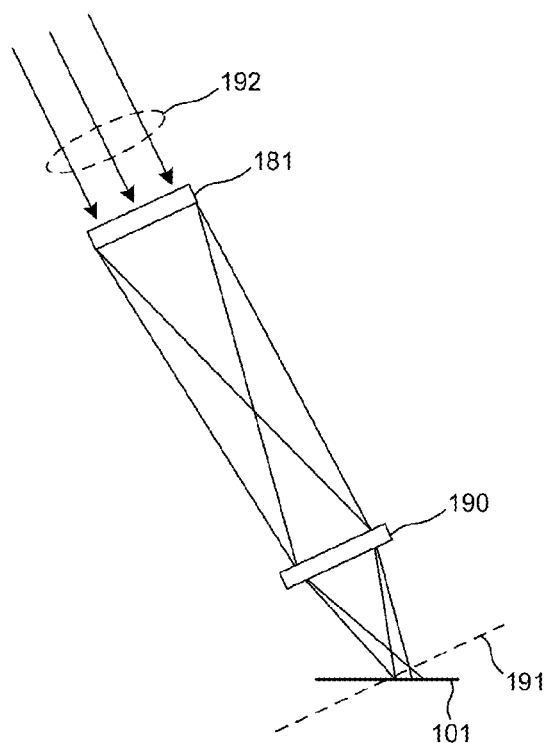
FIG. 10 depicts an amount of illumination light 192 entering an illumination slit 181 that is oriented perpendicular to the optical axis of the illumination beam.

FIG. 10 depicts an amount of illumination light 192 that enters an illumination slit 181 that is oriented perpendicular to the optical axis of the illumination beam before entering the illumination objective 190. The optical axis of the illumination light is oriented at an obilique angle with respect to the surface of specimen 101. In some examples, the optical axis of the illumination light is oriented at an angle of approximately 65 degrees with respect to an axis normal to the surface of specimen 101. The illumination system depicted in FIG. 10 results in a focal plane 191 that is not aligned with the surface of specimen 101. This leads to a blur of the image of the illumination slit 181 on the surface of specimen 101 and this blur results in an effective increase in illumination spot size.

Figure 11:
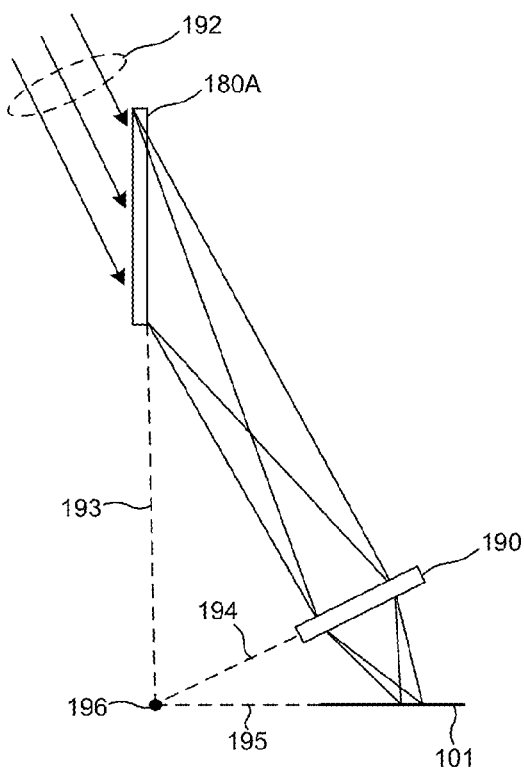
FIG. 11 depicts an amount of illumination light 192 entering an illumination aperture having an image plane oriented at an oblique angle with respect to the optical axis of the illumination beam.

FIG. 11 depicts an illumination system having an illumination aperture (e.g., illumination slit 180A) that is oriented amount of illumination light 192 that enters an illumination slit 181 that is oriented at an oblique angle with respect to the optical axis of the beam of illumination light entering objective 190. In some embodiments, illumination aperture 180 is oriented such that the image plane 193 of illumination aperture 180A, the principal plane 194 of objective lens 190, and the surface plane 195 of specimen 101 intersect along a common line 196. This configuration satisfies the Scheimpflug condition. The Scheimpflug condition identifies that if either the object plane (e.g., surface of specimen 101) or the image plane (e.g., image plane of illumination aperture 180 is tilted with respect to one another, the distances of both the object and image to the principal plane of the imaging system (e.g., objective 190) need to change depending on the object height to satisfy the geometrical image condition for all field heights. As depicted in FIG. 11, with the orientation of the image plane of illumination aperture 180A satisfying the Scheimpflug condition, the illumination aperture is imaged onto the surface of specimen 101 without blur (i.e., in focus over the entire field). This results in an effective decrease in illumination spot size.

Figure 12:
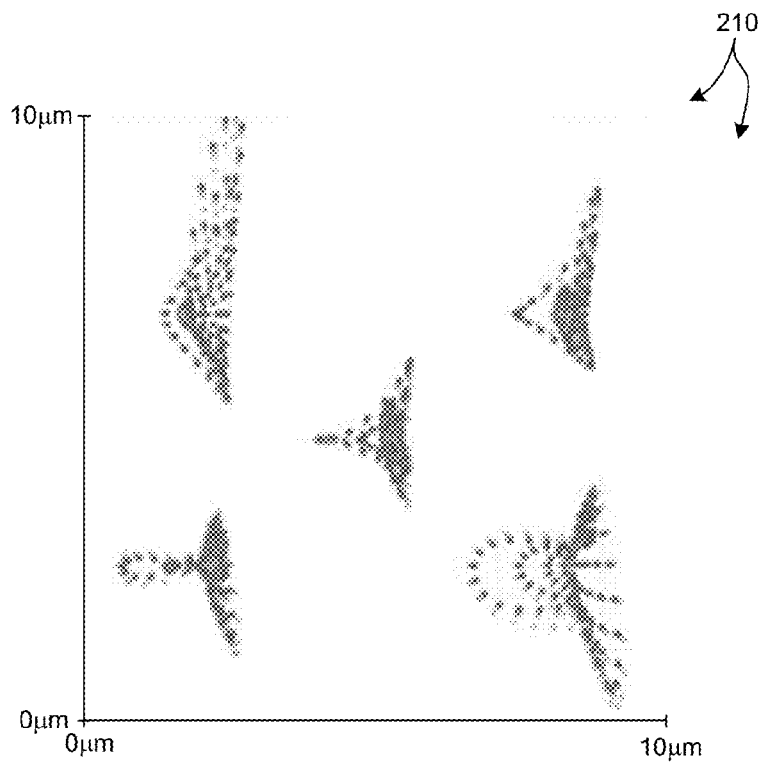
FIG. 12 depicts measurement simulation results of the projection of field points at the center and four corners of a rectangular illumination slit oriented perpendicular to an optical axis of the beam of illumination light entering the system objective.

FIG. 12 depicts measurement simulation results of a metrology system (SpectraShape 10000 manufactured by KLA-Tencor Corp., Milpitas, Calif. (USA)) depicting the projection of field points at the center and four corners of a rectangular illumination slit oriented perpendicular to optical axis of the beam of illumination light entering the system objective. Note the presence of relatively large spatial distributions of light, particularly at the corners where blur is most visible.

Figure 13:
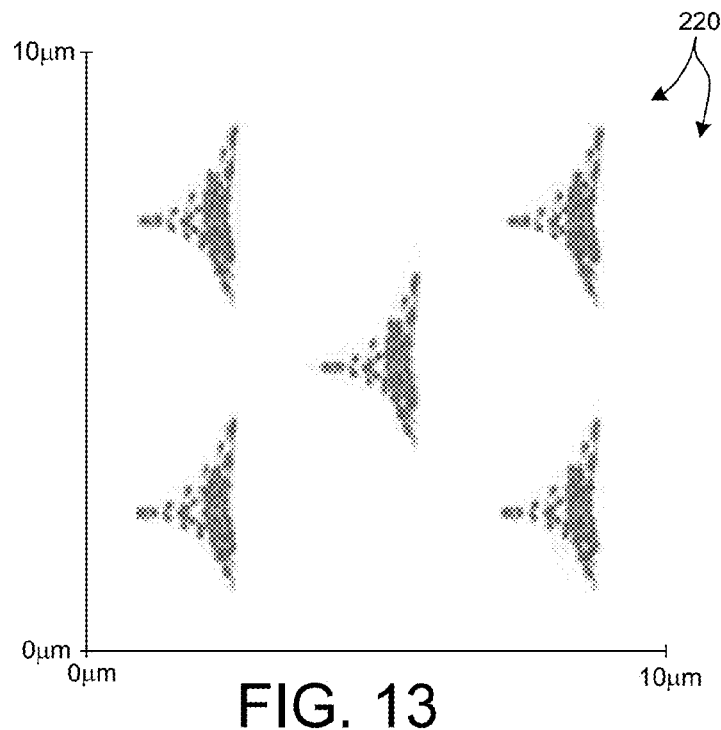
FIG. 13 depicts measurement simulation results of the same metrology system as described with reference to FIG. 12, except that the illumination slit is oriented at an oblique angle with respect to the optical axis of the beam of illumination light entering the system objective.

FIG. 13 depicts measurement simulation results of the same metrology system as described with reference to FIG. 12, except that the illumination slit is oriented at an oblique angle with respect to the optical axis of the beam of illumination light entering the system objective in accordance with the Scheimpflug condition. Note the relatively uniform spatial distributions of light across the field, and the relatively small size of the distributions compared to FIG. 12.

Image quality for an optical system includes considerations of diffraction, aberrations, and geometric boundaries for electric field transfer from an object to an image. For the metrology systems discussed herein, optical image quality correlates to minimal effective illumination spot size with respect to the projected geometric boundaries. An ideal system would produce an image of the illumination aperture with no electric field beyond the projected geometric boundaries. To minimize the effective illumination spot size, the illumination aperture should be located in the path of the beam of illumination light that results in optimal image quality and thus minimizes the fraction of energy outside of the projected geometric boundaries (i.e., minimizes the size of the actual image with respect to the projected geometric image).

In general, the electric field transfer from an object to an image can be expressed in terms of the location of the object points (x,y,z), the location of the image points (x',y',z') and the associated wave vector components for the object ($k_x$, $k_y$, $k_z$) and image ($k'_x$, $k'_y$, $k'_z$). The focal plane on the entrance pupil side is defined at z=0, and the focal plane on the exit pupil side is defined at z'=0. The chief ray intersects the entrance focal plane at (x,y,z)=(0,0,0) and intersects the exit pupil plane at (x',y',z')=(0,0,0). Using these definitions and noting that both the object and the corresponding image are near the focus of the object plane and corresponding image plane, the phase for propagation from the object to the entrance pupil sphere is expressed by equation (1), $$\text{Object Phase}(x, y, z) = k_x x + k_y y + k_z z = \frac{2\pi}{\lambda}(NA_x x + NA_y y + NA_z z) \quad (1)$$

where, $$NA_z = \sqrt{1 - NA_x^2 - NA_y^2} \quad (2)$$

For NA less than or equal to 0.50, equation (2) can be approximated as $$NA_z \approx 1 - \frac{NA_x^2}{2} - \frac{NA_y^2}{2} \quad (3)$$

and equation (1) can be approximated by equation (4).

$$\text{Object Phase}(x, y, z) \approx \frac{2\pi}{\lambda}\left[NA_x x + NA_y y + z\left(-\frac{NA_x^2}{2} - \frac{NA_y^2}{2}\right)\right] + z\frac{2\pi}{\lambda} \quad (4)$$

The phase for propagation from the exit pupil sphere to the image is expressed by equation (5).

$$\text{Image Phase}(x', y', z') = \quad (5)$$
$$\frac{2\pi}{\lambda}(NA'_x x' + NA'_y y' + NA'_z z') + W'(NA'_x x + NA'_y y)$$

where, $$NA'_z = \sqrt{1 - NA_x'^2 - NA_y'^2} \quad (6)$$

For NA' less than or equal to 0.50, equation (6) can be approximated as $$NA'_z \approx 1 - \frac{NA_x'^2}{2} - \frac{NA_y'^2}{2} \quad (7)$$

and equation (5) can be approximated by equation (8).

$$\text{Image Phase}(x', y', z') = \frac{2\pi}{\lambda}\left[NA'_x x' + NA'_y y' + z'\left(-\frac{NA_x^2}{2} - \frac{NA_y^2}{2}\right) + \quad (8)$$
$$W'\{x', y', NA'_x(x', y'), NA'_y(x', y')\}\right] + z\frac{2\pi}{\lambda}$$

Aberrations are included as $W\{x', y', NA'_x(x', y'), NA'_y(x', y')\}$ in the image phase expression. The magnification factor from the image to the object, m', is related to the magnification factor from the object to the image, m, by the relationship, m'=1/m. If the magnification factor is isotropic, then x=m'x', y=m'y', $NA_x$=$NA'_x$/m', and $NA_y$=$NA'_y$/m'.

From an object point (x,y,z) to an image point (x',y',z'), the image quality will depend only on the phase difference between different optical paths or, equivalently, different wave vectors. The Object Phase Change (OPC) is expressed by equation 9 and the Image Phase Change (IPC) is expressed by equation 10.

$$OPC(x, y, z) = \frac{2\pi}{\lambda}\left[NA_x x + NA_y y + z\left(-\frac{NA_x^2}{2} - \frac{NA_y^2}{2}\right)\right] \quad (9)$$

$$IPC(x', y', z') = \frac{2\pi}{\lambda}\left[NA'_x x' + NA'_y y' + z'\left(-\frac{NA_x'^2}{2} - \frac{NA_y'^2}{2}\right)\right] + \quad (10)$$
$$W(x', y', NA'_x(x', y'), NA'_y(x', y'))$$

If the target position of the image is the exit pupil focal plane and the aberration function, W, is equal to zero, $$OPC(X, Y, Z) = IPC(x', y', z') \quad (11)$$

$$IPC(x', y', z' = 0) = \frac{2\pi}{\lambda}(NA'_x x' + NA'_y y') = \quad (12)$$
$$\frac{2\pi}{\lambda}\left(\frac{NA'_x}{m'}m'x' + \frac{NA'_y}{m'}m'y'\right) = \frac{2\pi}{\lambda}(NA_x X + NA_y Y)$$

$$OPC(x', y', z' = 0) = \frac{2\pi}{\lambda}(NA_x X + NA_y Y + NA_z Z) \quad (13)$$

where, X=m'x', Y=m'y', and Z=0.

As expected, the optimal object position for an image in the exit focal plane is in the entrance focal plane.

For an image point not in the exit pupil focal plane and the aberration function, W, equal to zero, the optimal position of the corresponding object is $$OPC(X, Y, Z) = IPC(x', y', z') \quad (14)$$

$$IPC(x', y', z') \approx \frac{2\pi}{\lambda}\left[NA_x X + NA_y Y + z'm'^2\left(-\frac{NA_x^2}{2} - \frac{NA_y^2}{2}\right)\right] \quad (15)$$

$$OPC(x', y', z') \approx \frac{2\pi}{\lambda}\left[NA_x X + NA_y Y + Z\left(-\frac{NA_x^2}{2} - \frac{NA_y^2}{2}\right)\right] \quad (16)$$

where X=m'x', Y=m'y', and Z=z'm'$^2$.

If the image plane (e.g., surface of the specimen under measurement) is tilted with respect to the exit focal plane, then the image plane can expressed as a function of x',y', and z'. For example, if the specimen is tilted at an angle of incidence (AOI) in the x' direction, then the image plane coordinate z'=x' tan(AOI). If the aberration function, W, equals zero, the optimal position of the corresponding object can be estimated from equations (14)-(16) as $$OPC(x', y', z') \approx \quad (17)$$
$$\frac{2\pi}{\lambda}\left[NA_x X + NA_y Y + X\tan(AOI_{Obj})\left(-\frac{NA_x^2}{2} - \frac{NA_y^2}{2}\right)\right]$$

where X=m'x', Y=m'y', Z=X tan(AOI)m', $AOI_{obj}$=arctan(tan(AOI)m'), and the slit dimension is X/cos($AOI_{obj}$) by Y.

Figure 14:
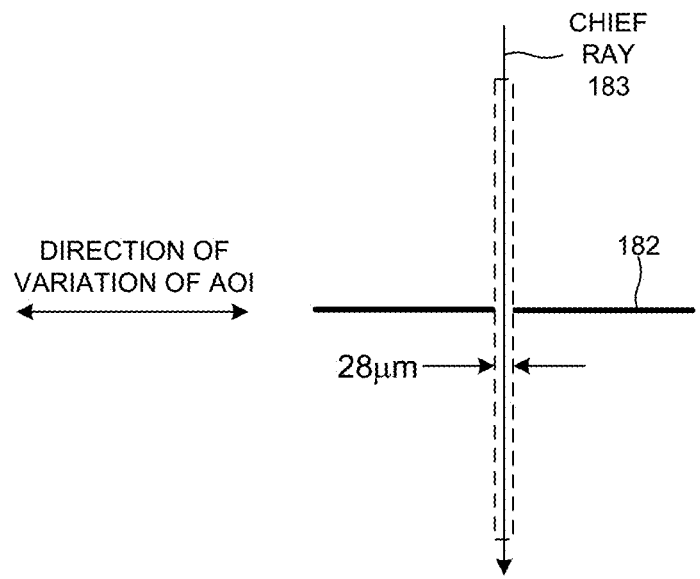
FIG. 14 depicts an illumination aperture 182 having rectangular dimensions of 100 µm×28 µm and oriented perpendicular to the chief ray 183 of the beam of illumination light.

FIG. 14 depicts an illumination aperture 182 (e.g., polarizer slit) having rectangular dimensions of 100 μm×28 μm. As depicted in FIG. 14, the illumination aperture 182 is oriented perpendicular to the chief ray 183 of the beam of illumination light.

Figure 15:
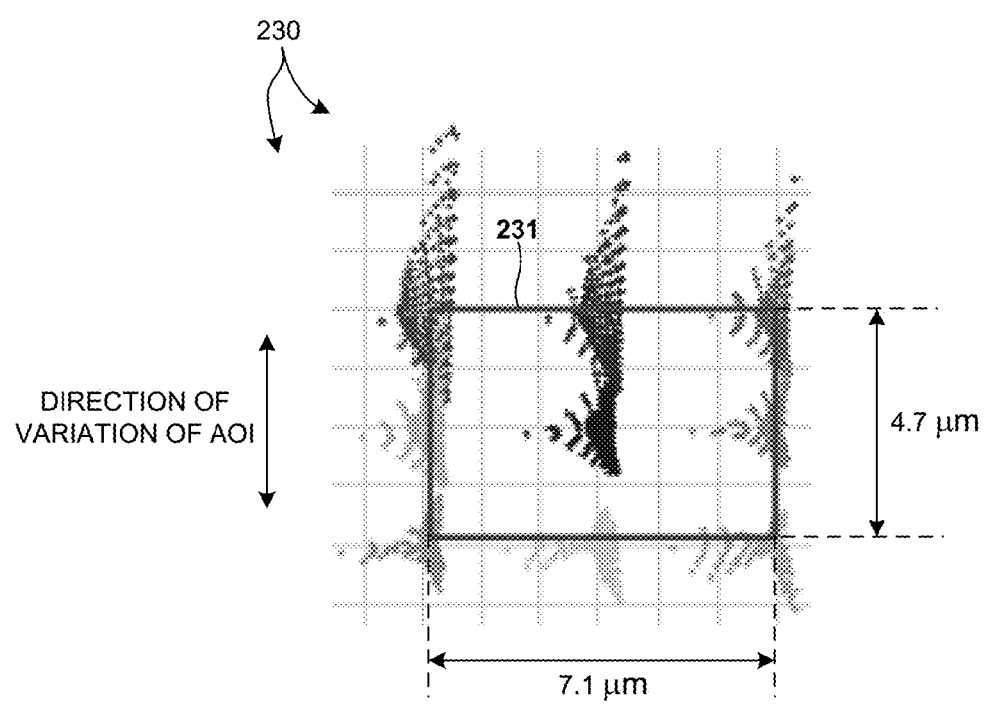
FIG. 15 depicts measurement simulation results depicting the projection of field points of illumination aperture 182 depicted in FIG. 14 at the center and four corners of the illumination aperture for an illumination angle of incidence of 65 degrees.

FIG. 15 depicts a plot 230 of measurement simulation results of a metrology system (SpectraShape 10000 manufactured by KLA-Tencor Corp., Milpitas, Calif. (USA)) depicting the projection of field points of illumination aperture 182 depicted in FIG. 14 at the center and four corners of the rectangular polarizer slit for an illumination AOI of 65 degrees and m'=14. The rectangle 231 depicted in FIG. 15 illustrates the geometric (i.e., ideal) projection of illumination aperture 182 onto the surface of a specimen. Note the presence of relatively large spatial distributions of light, particularly at the corners where blur is most visible.

Figure 16:
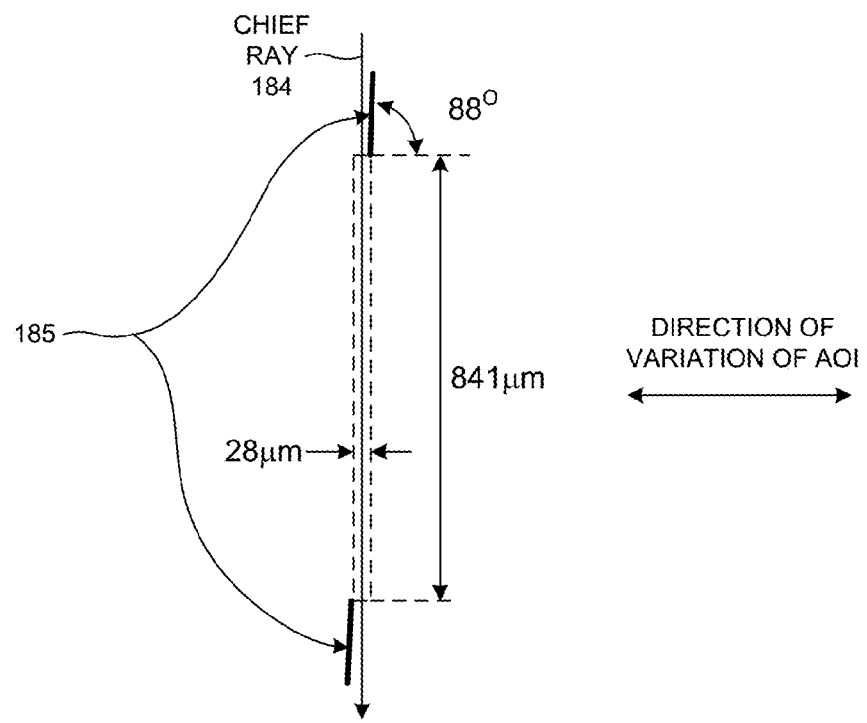
FIG. 16 depicts an illumination aperture 185 having rectangular dimensions of 100 µm×841 µm and oriented at 2 degrees with respect to the chief ray 184 of the beam of illumination light.

FIG. 16 depicts an illumination aperture 185 (e.g., polarizer slit) having rectangular dimensions of 100 μm×841 μm. As depicted in FIG. 16, the illumination aperture 185 is oriented at 2 degrees with respect to the chief ray 184 of the beam of illumination light (i.e., 88 degrees from perpendicular to chief ray 184).

Figure 17:
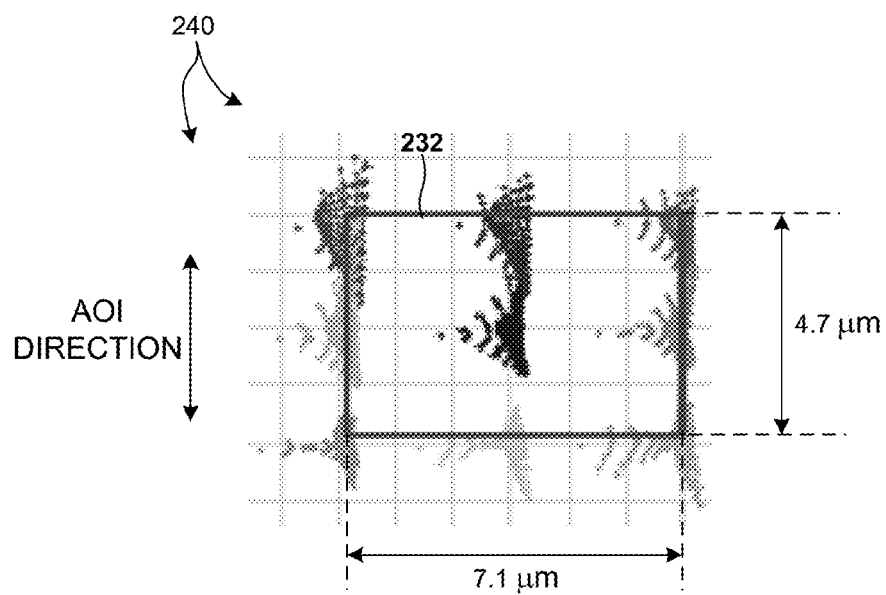
FIG. 17 depicts measurement simulation results depicting the projection of field points of illumination aperture 185 depicted in FIG. 16 at the center and four corners of the rectangular polarizer slit for an illumination angle of incidence of 65 degrees.

FIG. 17 depicts a plot 240 of measurement simulation results of a metrology system (SpectraShape 10000 manufactured by KLA-Tencor Corp., Milpitas, Calif. (USA)) depicting the projection of field points of illumination aperture 185 depicted in FIG. 16 at the center and four corners of the rectangular polarizer slit for an illumination AOI of 65 degrees and m'=14. The rectangle 232 depicted in FIG. 17 illustrates the geometric (i.e., ideal) projection of illumination aperture 185 onto the surface of a specimen. Note the uniformity of the spatial distributions of light across the field, and the relatively small spatial distributions of light compared to the results depicted in FIG. 15 for a polarizer slit oriented perpendicular to the illumination beam.

Figure 18:
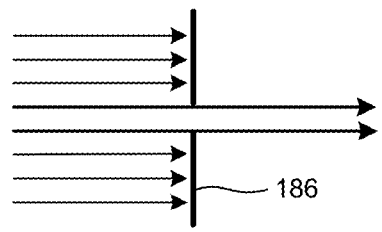
FIG. 18 depicts an illumination aperture 186 having an image plane oriented perpendicular to a beam of incoming light.
Figure 19:
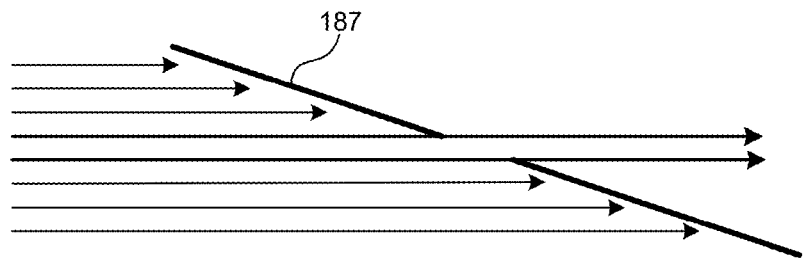
FIG. 19 depicts an illumination aperture 187 having an image plane oriented at an oblique angle with respect to a beam of incoming light.
Figure 20:
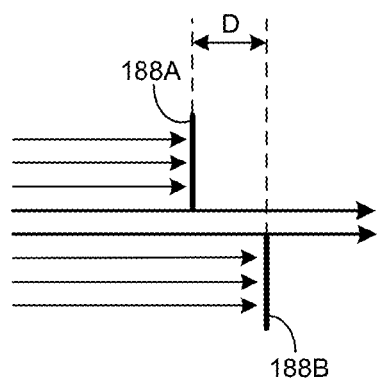
FIG. 20 depicts a stacked illumination aperture including two apertures 188A and 188B separated by a distance, D, that in combination result in illumination aperture having an image plane oriented at an oblique angle with respect to a beam of incoming light.
Figure 21:
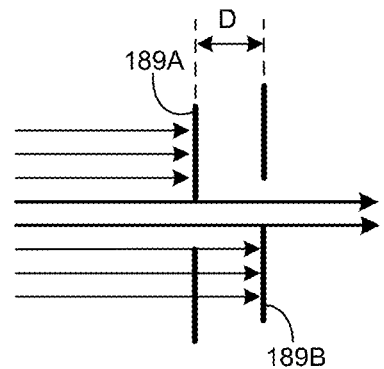
FIG. 21 depicts a stacked illumination aperture including two apertures 188A and 188B separated by a distance, D, that in combination result in illumination aperture having an image plane oriented at an oblique angle with respect to a beam of incoming light.

FIG. 18 depicts an illumination aperture 186 having an image plane oriented perpendicular to a beam of incoming light. FIG. 19 depicts an illumination aperture 187 having an image plane oriented at an oblique angle with respect to a beam of incoming light. FIG. 20 depicts a stacked illumination aperture including two apertures 188A and 188B separated by a distance, D, that in combination result in illumination aperture having an image plane oriented at an oblique angle with respect to a beam of incoming light. Similarly, FIG. 21 depicts a stacked illumination aperture including two apertures 188A and 188B separated by a distance, D, that in combination result in illumination aperture having an image plane oriented at an oblique angle with respect to a beam of incoming light. In general, an illumination aperture may be include any number of different stacked apertures or be configured as a continuum aperture element.

Figure 22:
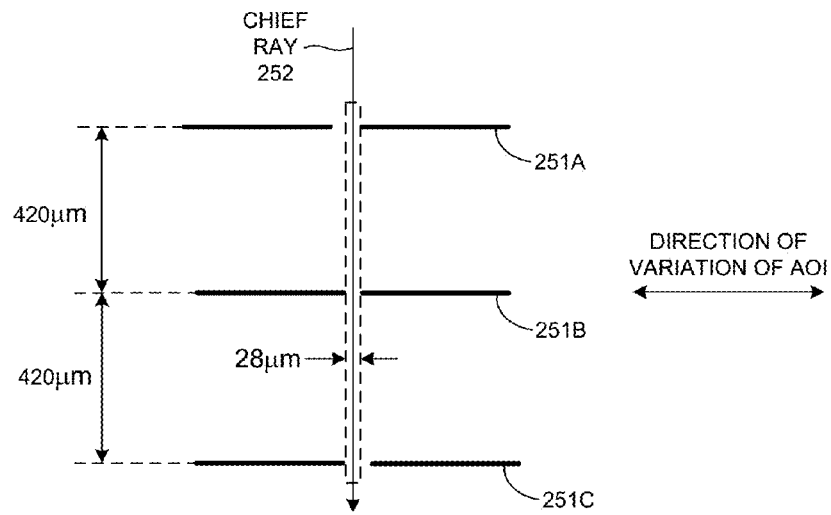
FIG. 22 depicts a stacked illumination aperture having three stacked apertures 251A-C, each separated by 420 micrometers.

For a stacked illumination aperture, equation (17) applies. FIG. 22 depicts a stacked illumination aperture (e.g., polarizer slit) having three stacked apertures 251A-C, each separated by 420 micrometers. As depicted in FIG. 22, the each of the stacked apertures 251A-C are oriented perpendicular to the chief ray 252 of the beam of illumination light. However, in combination, the image plane of the illumination aperture formed by stacked apertures 251A-C is oriented at 2 degrees with respect to chief ray 252 (i.e., 88 degrees from perpendicular to chief ray 252).

Figure 23:
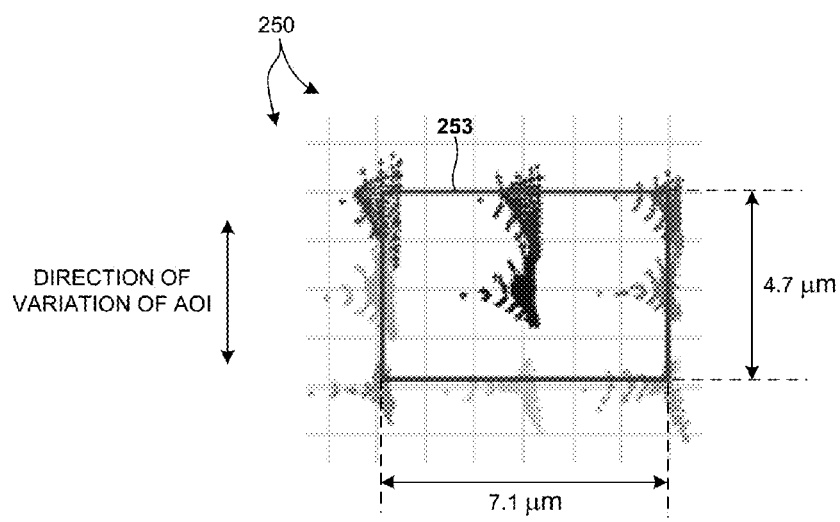
FIG. 23 depicts the projection of field points of the illumination aperture formed from stacked apertures 251A-C depicted in FIG. 22 at the center and four corners of the geometric projection of the illumination aperture onto a specimen for an illumination AOI of 65 degrees.

FIG. 23 depicts a plot 250 of measurement simulation results of a metrology system (SpectraShape 10000 manufactured by KLA-Tencor Corp., Milpitas, Calif. (USA)) depicting the projection of field points of the illumination aperture formed from stacked apertures 251A-C depicted in FIG. 22 at the center and four corners of the geometric projection of the illumination aperture onto a specimen for an illumination AOI of 65 degrees and m'=14. The rectangle 253 depicted in FIG. 23 illustrates the geometric (i.e., ideal) projection of the illumination aperture formed from stacked apertures 251A-C onto the surface of a specimen. Note the uniformity of the spatial distributions of light across the field, and the relatively small spatial distributions of light compared to the results depicted in FIG. 15 for a polarizer slit oriented perpendicular to the illumination beam.

For an image point not in the exit pupil focal plane and a non-zero aberration function, the optimal position of the corresponding object is calculated by minimizing the phase difference given by equation (18).

$$PhaseDifference = \left| \frac{2\pi}{\lambda} \left[ (z'm'^2 - Z)\left(-\frac{NA_x^2}{2} - \frac{NA_y^2}{2}\right) + W\{X, Y, NA_x(X, Y), NA_y(X, Y)\} \right] \right| \quad (18)$$

For any given set of parameters $\{z', X, Y, NA_x, \text{and } NA_y\}$, the value of Z which minimizes phase difference can be determined numerically or, for some functions, analytically. Since the value of Z depends on $NA_x$ and $NA_y$, the optimal value of Z for the image for all $NA_x$ and $NA_y$ can be determined using modern ray trace optical software which includes all surfaces and aberrations in a complete model of the optical system. In some examples, the optimization process employs the optimal, aberration-free object position as a starting point in the optimization, and optimizes the position of the aperture or slit to minimize projected energy outside of an image boundary.

Figure 29:
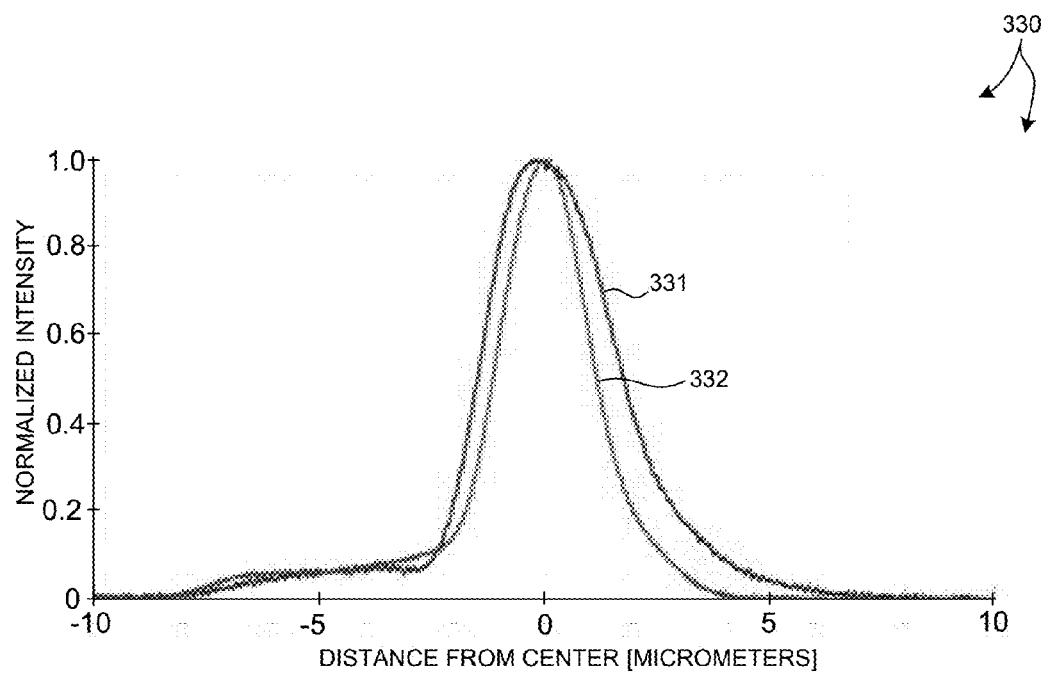
FIG. 29 illustrates a plot 330 illustrative of a measured reduction in illumination spot size due the use of a tilted illumination aperture in one example.

FIG. 29 illustrates a plot 330 illustrative of a measured reduction in illumination spot size due the use of a tilted illumination aperture as described herein. Plot 330 depicts the projection of illumination light from a laser based light source onto a specimen under measurement by illumination optics. Plotline 331 depicts the intensity distribution across the illumination beam at the point of incidence with a specimen under measurement when the illumination optics includes a polarizer slit having an image plane oriented perpendicular to the beam of incoming light as described with reference to FIGS. 10, 12, and 14-15. Plotline 332 depicts the intensity distribution across the illumination beam at the point of incidence with a specimen under measurement when the illumination optics includes a polarizer slit having an image plane oriented at an oblique angle with respect to a beam of incoming light as described with reference to FIGS. 11, 13, 16, 17, and 24A-B.

Figure 30:
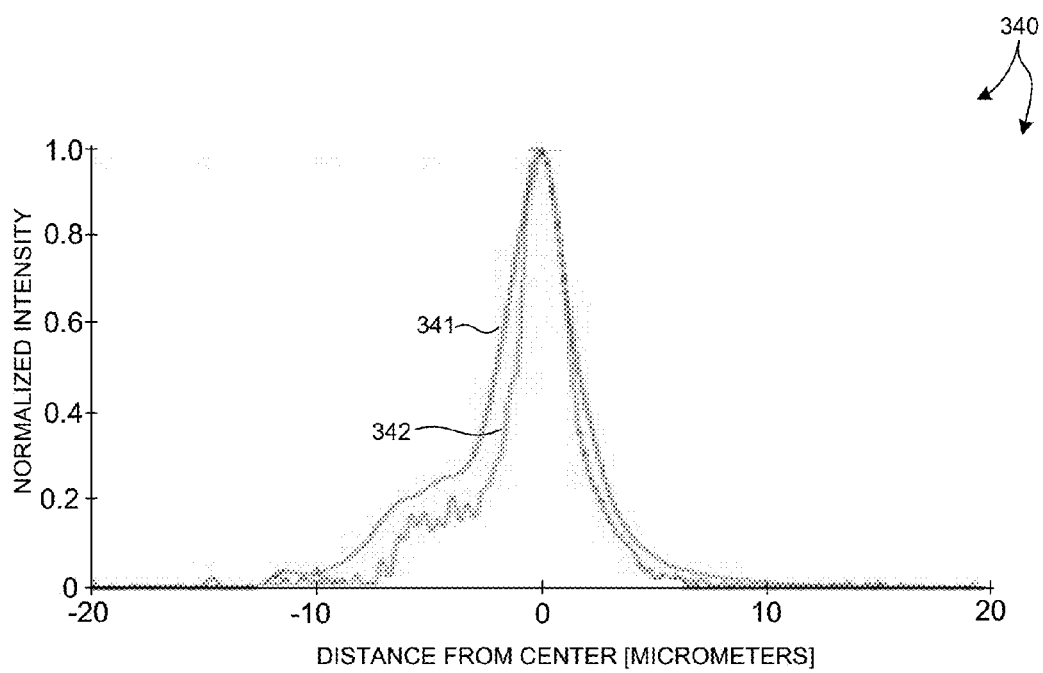
FIG. 30 illustrates a plot 340 illustrative of a measured reduction in illumination spot size due the use of a tilted illumination aperture in another example.

FIG. 30 illustrates a plot 340 illustrative of a measured reduction in illumination spot size due the use of a tilted illumination aperture as described herein. Plot 340 depicts the projection of illumination light from a LDLS onto a specimen under measurement by illumination optics. Plotline 341 depicts the intensity distribution across the illumination beam at the point of incidence with a specimen under measurement when the illumination optics includes a polarizer slit having an image plane oriented perpendicular to the beam of incoming light as described with reference to FIGS. 10, 12, and 14-15. Plotline 342 depicts the intensity distribution across the illumination beam at the point of incidence with a specimen under measurement when the illumination optics includes a polarizer slit having an image plane oriented at an oblique angle with respect to a beam of incoming light as described with reference to FIGS. 11, 13, 16, 17, and 24A-B. In the experiments described with reference to FIGS. 29 and 30, a reduction of illumination spot size of approximately 35% is achieved.

An illumination aperture having an image plane tilted at an oblique angle with respect to the beam of illumination light may be implemented in a number of different ways.

In some embodiments, a single, thin illumination slit (e.g., polarizer slit) is tilted at an oblique angle with respect to an illumination beam, as described with reference to FIGS. 16-17 and 19. In some embodiments, the slit may be supported at the appropriate angle by a holder fabricated by machining, three dimensional printing, etc.

Figure 24A:
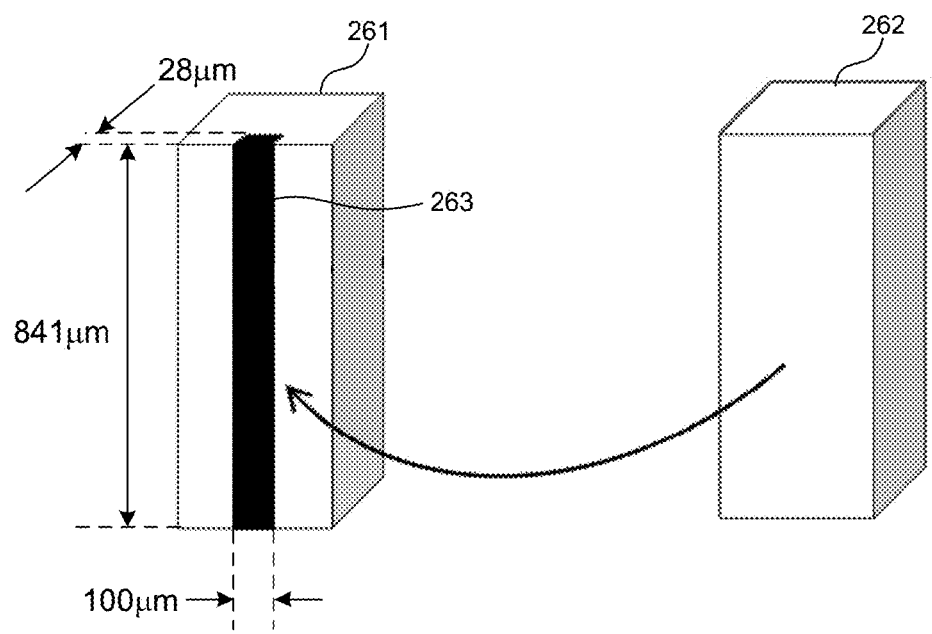
FIGS. 24A-24B depict a thick illumination slit fabricated from two blocks.
Figure 24B:
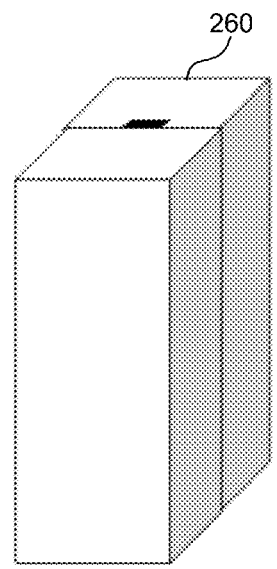

In some other embodiments, a thick illumination slit may be employed. FIG. 24B depicts a specific example of a thick illumination slit 260 fabricated from two blocks depicted in FIG. 24A. As depicted in FIG. 24A, a trench feature 263 that is 100 micrometers wide, 28 micrometers thick, and 841 micrometers long is machined from block 261. Block 262 is fastened to the face of block 261 to cover the exposed trench feature 263 and form thick illumination slit 260 depicted in FIG. 24B. In some embodiments, the thick slit feature could be fabricated by modeling the thick slit feature with a sacrificial material (e.g., Aluminum), growing another material around the sacrificial material, and then etching away the sacrificial material to realize the desired thick slit feature. In general, the thick slit feature can be fabricated by any one or combination of manufacturing techniques such as sandwiching, gluing, electro-discharge machining, laser machining, laser drilling, and laser welding, etc.

In general, it is beneficial to reduce internal reflections from the inner walls of a thick illumination slit. Thus, it may be useful to blacken, anodize, curve, reshape, roughen, or otherwise deform the surfaces of the inner walls of the thick slit.

Figure 25A:
FIGS. 25A-D depict different cross-sections 270-273, respectively, of a thick illumination slit.
Figure 25B:
Figure 25C:
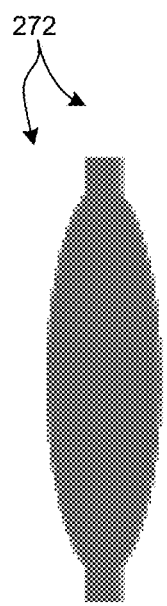
Figure 25D:

In general, the shape of the cross-section of the thick slit along the length dimension (i.e., the direction aligned with the beam of illumination light) does not have to be rectangular. FIGS. 25A-D depict different cross-sections 270-273, respectively, of a thick illumination slit. The cross-sections depicted in FIGS. 25A-D are provided by way of non-limiting example. For example as depicted in FIG. 25C, the use of elliptical slits might be beneficial to reduce undesired edge effects arising from the corners of the rectangle. In general, any other shape may be contemplated.

In some other embodiments, a stack of two or more slits may be employed as described with reference to FIGS. 21-23. The alignment of a stack of illumination slits may be achieved by aligning the stacks on the metrology system itself to maximize the amount of light throughput. Registration features may be introduced on the material around the illumination slit and shims or other mechanical features may be employed to control the separation between adjacent illumination slits. Illumination slits may be fabricated on opposite faces of a glass substrate by printing, deposition, or other forms of precision manufacturing.

In general, an illumination slit or combination of slits may be formed by laser cutting, etching lithography, electro-discharge machining (EDM), milling, drilling, three dimensional printing, or other printing methods.

In a further aspect, an illumination aperture is configured to be adjustable and programmable. In some embodiments, a turret assembly includes a number of different illumination apertures each having an image plane oriented at an oblique angle with respect to the illumination beam when located in the path of the beam. Depending on the system requirements the turret may be controlled by a computing system (e.g., computing system 130) to locate the appropriate illumination aperture into the path of the illumination beam. In some embodiments, an illumination aperture may include adjustable mechanical features that can be flexibly positioned to change the size of an aperture, orientation angle, separation of multiple aperture elements, alignment of aperture elements, etc. In these embodiments, the illumination aperture may be controlled by a computing system (e.g., computing system 130) to configure the adjustable illumination aperture to achieve the desired size, shape, location, orientation, alignment, etc. In some other embodiments, an illumination slit may be fabricated from a programmable material (e.g., nano-material, self-assembling material, etc.). In some other embodiments, an illumination aperture may be based on a spatial light modulation device (e.g., a micro-electro-mechanical device, a liquid crystal device, a programmable reflective mirror device, etc.).

In general, a variety of metrology system architectures benefit from a reduced measurement box size enabled by a spatial light modulator located in an illumination path, an illumination aperture having an image plane oriented at an oblique angle with respect to the illumination beam, or a combination of both. In one example, spherical-optics based scatterometer systems employing reflective optics benefit from the improved illumination techniques as described herein. Both ellipsometer and reflectometer configurations may benefit from a spatial light modulator located in an illumination path, an illumination aperture having an image plane oriented at an oblique angle with respect to the illumination beam, or a combination of both. In some embodiments a metrology system includes an ellipsometer module as described herein, along with a normal-incidence reflectometer where the reflectometer also includes a spatial light modulator (e.g., a deformable mirror) in the illumination path. In some examples, the reflectometer is based on an aspheric optics design. In some other examples, the reflectometer is based on a spherical optics design. In some embodiments, an illumination source is shared between the ellipsometer and the reflectometer of the combined metrology system. In some embodiments, multiple illumination sources are utilized to achieve a broad spectral range (e.g., a laser-driven plasma source for shorter wavelengths and a supercontinuum laser source for longer wavelengths). In some embodiments, a metrology system includes multiple ellipsometers, each configured to perform simultaneous measurements at different azimuth angles.

Figure 31:
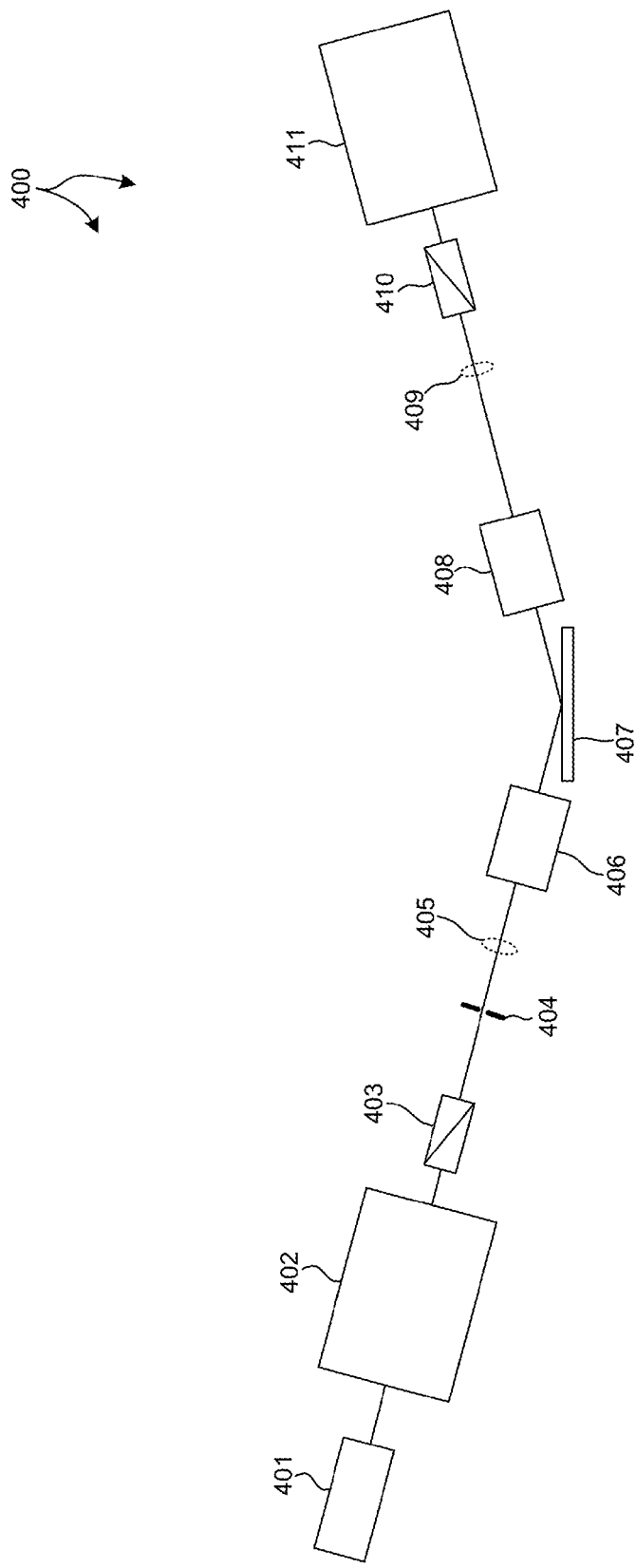
FIG. 31 depicts an exemplary metrology system 400 that includes a spatial light modulator 405 located in an illumination path and an illumination aperture 406 having an image plane oriented at an oblique angle with respect to the illumination beam.

FIG. 31 depicts an exemplary metrology system 400 that includes an illuminator 402 with a spatial light modulator located in an illumination path and an illumination aperture 404 having an image plane oriented at an oblique angle with respect to the illumination beam as described herein. Metrology system 400 is a broadband spectroscopic ellipsometer (BBSE) having an illumination source 401 that includes both a laser driven light source (LDLS) and a mercury-xenon lamp configured to provide illumination light to the spectroscopic ellipsometer over a broad range of wavelengths. In one aspect, BBSE 400 does not include transmissive optical elements in either the illumination or collection objectives. Employing only reflective optical elements improves illumination efficiency and increases measurement sensitivity, particularly at shorter wavelengths. Light emitted from the LDLS 401 and mercury-xenon lamp is directed to illuminator 402 that includes a deformable mirror (DM). The DM is configured to modulate the amplitude and phase distribution across the path of the illumination light to reduce wavefront errors as described herein. With wavefront correction, a smaller measurement box size is achieved than would otherwise be possible if the wavefront errors were left uncorrected. The modulated beam of illumination light passes through Rochon polarizer 403 and polarizer slit 404. Polarizer slit 404 has an image plane that is tilted at an oblique angle with respect to the beam of illumination light to overcome defocusing effects that arise from oblique illumination of the measurement sample. In the depicted embodiment, the illumination aperture is oriented such that the image plane of the illumination aperture, the principal plane of the objective lens, and the surface plane of the specimen under measurement intersect along a common line. This configuration satisfies the Scheimpflug condition and under this condition the illumination aperture is imaged onto the surface of specimen 407 without blur. After passing through polarizer slit 404, the polarized beam of illumination light 405 is focused by illumination objective 406 onto specimen 407. A portion of the light reflected, refracted, diffracted, and scattered from the surface of specimen 407 is collected by a collection objective 408. The beam of collected light 409 passes through Rochon analyzer 410 and is incident on one or more detectors of spectrometer 411.

In a further embodiment, BBSE 400 also includes rotating compensator elements located in one or both of the illumination and collection paths. This enables BBSE 400 to perform Mueller Matrix measurements of specimen 407.

In many examples, the primary focus is to achieve a small metrology box size for metrology architectures with multiple angles of incidence using the methods and apparatus described herein. These include but are not limited to multiple-AOI spectroscopic ellipsometry (SE) in its standard or Mueller matrix (MMSE) implementations, multiple-AOI spectroscopic reflectometry, beam profile reflectometry (BPR), single wavelength ellipsometry, beam profile ellipsometry (BPE), with BPR or BPE technologies used in either one-dimensional or two-dimensional angle-resolved implementations, angle resolved scatterometry, and spectroscopic scatterometry.

However, in general the methods and apparatus described herein are compatible with all known optical metrology tools individually, or in combination as part of a combined measurement analysis. Such optical metrology techniques include, by way of non-limiting example, spectroscopic ellipsometry, spectroscopic reflectometry, angle-resolved reflectometry and ellipsometry, spectroscopic scatterometry, scatterometry overlay, beam profile reflectometry, (angle and polarization resolved), beam profile ellipsometry, single or multiple discrete wavelength ellipsometry, multiple angle of incidence ellipsometry, and spectroscopic polarimetry, etc. In general, any metrology technique applicable to the characterization of semiconductor structures, including image based metrology techniques, may be contemplated.

In some examples, the apparatus and methods described herein to achieve a small size measurement box may be used in conjunction with existing focused beam ellipsometer systems such as described by 1) U.S. Pat. No. 5,608,526 entitled "Focused beam spectroscopic ellipsometry method and system," issued Mar. 4, 1997, to KLA-Tencor Corporation, the contents of which are incorporated by reference as if fully set forth herein, and 2) U.S. Pat. No. 5,859,424 entitled "Apodizing filter system useful for reducing spot size in optical measurements and other applications," issued Jan. 12, 1999, to KLA-Tencor Corporation, the contents of which are incorporated by reference as if fully set forth herein.

The methods and apparatus described herein to achieve a small metrology box size are useful for CD metrology, thin film metrology, shape metrology, and composition metrology. However, these applications are not limiting, the methods described herein are also useful in overlay metrology applications, pitchwalk measurement applications, focus and dosage monitoring applications, etch monitoring applications, lithography applications, etc.

As discussed hereinbefore, a SLM in the illumination path, an illumination aperture having an image plane oriented at an oblique angle with respect to the illumination light, or both, are utilized to achieve a small metrology box size as part of a metrology tool (e.g., metrology tool 100). However, these methods and apparatus to achieve a small metrology box size measurement capability may also be implemented as part of a fabrication process, and/or fabrication process tool. Examples of fabrication process tools include, but are not limited to, lithographic exposure tools, film deposition tools, implant tools, and etch tools. In this manner, measurement results are used to control a fabrication process. In one example, measurement data collected from one or more targets in accordance with the methods and apparatus described herein is used by a lithography tool to control focus and dosage. In another example, measurement data collected from one or more targets in accordance with the methods and apparatus described herein is used by an etch tool to control etch process parameters such as etch time.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including critical dimension applications and overlay metrology applications. However, such terms of art do not limit the scope of the term "metrology system" as described herein. In addition, the metrology system 100 may be configured for measurement of patterned wafers and/or unpatterned wafers. The metrology system may be configured as a LED inspection tool, solar inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media, and communication media, including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition, of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A metrology system comprising:
    an illumination source configured to generate an amount of illumination light;
    an illumination optics subsystem configured to direct the amount of illumination light from the illumination source to a specimen under measurement, wherein the illumination optics subsystem includes:
        a spatial light modulator disposed in a path of the illumination light from the illumination source to the specimen under measurement, wherein the spatial light modulator is configured to modulate amplitude, phase, or a combination of amplitude and phase across the path of the illumination light and generate a wavefront distortion over a portion of the illumination light that is same for all wavelengths of the amount of illumination light;
    a detector configured to generate a plurality of output signals indicative of a response of the specimen to the amount of illumination light; and
    a collection optics subsystem configured to collect an amount of collected light from the surface of the specimen and direct the amount of collected light to the detector.

2. The metrology system of claim 1, wherein the spatial light modulator is any of a deformable mirror device, a pixelated mirror device, a transmissive liquid crystal display device, and a reflective liquid crystal on silicon device.

3. The metrology system of claim 1, further comprising:
    a controller configured to:
        transmit a command signal to the spatial light modulator to alter a state of the spatial light modulator to achieve a desired amplitude profile, phase profile, or a combination of the amplitude profile and the phase profile across the path of the illumination light.

4. The metrology system of claim 3, further comprising:
    a wavefront sensor configured to measure amplitude, phase, or both amplitude and phase across the illumination light or across the collected light.

5. The metrology system of claim 4, wherein the controller is further configured to:
    receive an indication of a measurement of amplitude, phase, or both amplitude and phase across the illumination light by the wavefront sensor; and
    determine the desired amplitude profile, phase profile, or both the desired amplitude profile and the desired phase profile across the path of the illumination light based at least in part on the measurement of amplitude, phase, or both amplitude and phase across the illumination light by the wavefront sensor.

6. The metrology system of claim 3, wherein the wavefront sensor is disposed in the collection path.

7. The metrology system of claim 3, wherein the wavefront sensor is disposed in the illumination path.

8. The metrology system of claim 3, wherein the desired amplitude profile, phase profile, or both the desired amplitude profile and the desired phase profile across the path of the illumination light of the metrology system matches a desired amplitude profile, phase profile, or both the desired amplitude profile and the desired phase profile across the path of the illumination light of another metrology system or group of metrology systems.

9. The metrology system of claim 3, wherein the desired amplitude profile, phase profile, or combination of the amplitude profile and phase profile across the path of the illumination light is selected to match the amplitude profile, phase profile, or combination of the amplitude profile and phase profile of a reference metrology system.

10. The metrology system of claim 1, wherein a measurement box size of the metrology system is less than 30 micrometers in any direction.

11. The metrology system of claim 1, wherein a measurement box size of the metrology system is less than 10 micrometers in any direction.

12. The metrology system of claim 1, wherein the metrology system is an ellipsometer, wherein the amount of illumination light is directed to the specimen under measurement at one or more angles of incidence.

13. The metrology system of claim 12, wherein the ellipsometer is configured to perform Mueller Matrix measurements.

14. The metrology system of claim 1, wherein the metrology system is configured to perform any of film metrology, composition metrology, critical dimension metrology, shape metrology, and overlay metrology.

15. A method comprising:
receiving an amount of illumination light from an illumination source;
modulating an amplitude profile, a phase profile, or both the amplitude profile and the phase profile across a path of the illumination light from the illumination source to a surface of a specimen under measurement such that a wavefront distortion is generated over a portion of the illumination light that is same for all wavelengths of the amount of illumination light;
directing an amount of collected light from the surface of the specimen to a detector; and
generating a plurality of output signals from the collected light, wherein the output signals are indicative of a response of the specimen to the amount of modulated illumination light.

16. The method of claim 15, further comprising:
determining an estimate of a structural parameter based at least in part on the plurality of output signals.

17. The method of claim 15, further comprising:
determining a desired amplitude profile, phase profile, or both the desired amplitude profile and the desired phase profile of the modulated of the illumination light; and
transmitting a command signal to a spatial light modulator to alter a state of the spatial light modulator to achieve the desired amplitude profile, phase profile, or a combination of the amplitude profile and the phase profile.

18. The method of claim 17, further comprising:
measuring the amplitude, phase, or both the amplitude and the phase across the modulated illumination light or across the collected light, and wherein the determining the desired amplitude profile, phase profile, or both the desired amplitude profile and the desired phase profile is based at least in part on measured amplitude, phase, or both amplitude and phase.

19. The method of claim 15, wherein the modulating the phase profile across the path of the illumination light involves reflecting the illumination light from a deformable mirror having a programmable surface profile.

20. A metrology system comprising:
an illumination source configured to generate an amount of illumination light;
an illumination optics subsystem configured to direct the amount of illumination light from the illumination source to a specimen under measurement, the illumination optics subsystem including a spatial light modulator disposed in a path of the illumination light from the illumination source to the specimen under measurement, wherein the spatial light modulator is configured to modulate amplitude, phase, or a combination of amplitude and phase across the path of the illumination light and generate a wavefront distortion over a portion of the illumination light that is same for all wavelengths of the amount of illumination light;
a collection optics subsystem configured to collect an amount of collected light from the surface of the specimen and direct the amount of collected light to a detector;
a wavefront sensor configured to measure amplitude, phase, or both amplitude and phase across the illumination light or across the collected light; and
a computing system configured to:
receive an indication of the measurement of amplitude, phase, or both amplitude and phase by the wavefront sensor; and
transmit a command signal to the spatial light modulator to alter a state of the spatial light modulator to achieve a desired amplitude profile, phase profile, or a combination of the amplitude profile and the phase profile across the path of the illumination light based at least in part on the measurement of amplitude, phase, or both amplitude and phase by the wavefront sensor.

* * * * *